US012233178B2

(12) United States Patent
Childress

(10) Patent No.: US 12,233,178 B2
(45) Date of Patent: Feb. 25, 2025

(54) SYSTEMS AND METHODS OF VERIFYING EFFECTIVE MOTION OF A WAND ASSEMBLY OF AN ULTRAVIOLET (UV) LIGHT SANITIZING SYSTEM

(71) Applicant: THE BOEING COMPANY, Chicago, IL (US)

(72) Inventor: Jamie J. Childress, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 586 days.

(21) Appl. No.: 17/020,951

(22) Filed: Sep. 15, 2020

(65) Prior Publication Data

US 2022/0023478 A1 Jan. 27, 2022

Related U.S. Application Data

(60) Provisional application No. 63/055,389, filed on Jul. 23, 2020.

(51) Int. Cl.
*A61L 2/24* (2006.01)
*A61L 2/10* (2006.01)
(Continued)

(52) U.S. Cl.
CPC ...... *A61L 2/24* (2013.01); *A61L 2/10* (2013.01); *G01P 3/36* (2013.01); *G01S 17/58* (2013.01);
(Continued)

(58) Field of Classification Search
CPC ..... A61L 2/24; A61L 2/10; A61L 2/28; A61L 2202/11; A61L 2202/14; A61L 2202/16;
(Continued)

(56) References Cited

U.S. PATENT DOCUMENTS 6,630,105 B1 * 10/2003 O'Neill ................. A61L 2/202
95/47
8,105,532 B2 * 1/2012 Harmon ................. A61L 2/10
250/493.1
(Continued)

FOREIGN PATENT DOCUMENTS

CN 113616825 11/2021
EP 3915592 12/2021
(Continued)

OTHER PUBLICATIONS

Extended European Search Report for EP 21186441.8-1012, dated Dec. 20, 2021.
(Continued)

*Primary Examiner* — Regina M Yoo
(74) *Attorney, Agent, or Firm* — Joseph M. Butscher; The Small Patent Law Group LLC

(57) ABSTRACT

A system and a method include a wand assembly including a sanitizing head having an ultraviolet (UV) lamp configured to emit UV light to sanitize a surface of a component. The wand assembly further includes a first monitored member. The system also includes a second monitored member. A verification control unit is in communication with the first monitored member and the second monitored member. The verification control unit is configured to detect a speed of the wand assembly based on a comparison of the first monitored member in relation to the second monitored member.

25 Claims, 15 Drawing Sheets

(51) Int. Cl.
*G01P 3/36* (2006.01)
*G01S 17/58* (2006.01)

(52) U.S. Cl.
CPC ........ *A61L 2202/11* (2013.01); *A61L 2202/14* (2013.01); *A61L 2202/16* (2013.01); *A61L 2202/25* (2013.01)

(58) Field of Classification Search
CPC .......... A61L 2202/25; G01P 3/36; G01P 3/38; G01S 17/58; G01S 13/58; B64F 5/30; B64D 11/00
See application file for complete search history.

(56) References Cited

U.S. PATENT DOCUMENTS

| | | | |
|---|---|---|---|
| 10,874,756 | B1 | 12/2020 | Guerrero |
| 11,007,292 | B1 | 5/2021 | Grenon |
| 2008/0260601 | A1 | 10/2008 | Lyon |
| 2010/0104471 | A1 | 4/2010 | Harmon |
| 2011/0243789 | A1 | 10/2011 | Roberts |
| 2017/0216466 | A1* | 8/2017 | Dujowich ............. A61L 2/0047 |
| 2018/0117191 | A1 | 5/2018 | Shell |
| 2018/0117194 | A1 | 5/2018 | Dobrinsky |
| 2019/0030196 | A1 | 1/2019 | Bilenko |
| 2020/0215214 | A1 | 7/2020 | Rosen |
| 2021/0081749 | A1* | 3/2021 | Claire .................... G06F 3/167 |
| 2021/0299316 | A1 | 9/2021 | Mullen |
| 2021/0346541 | A1* | 11/2021 | Callahan .................. A61L 2/10 |
| 2021/0346561 | A1* | 11/2021 | Callahan .................. A61L 2/28 |
| 2021/0358621 | A1 | 11/2021 | Castle |
| 2021/0386882 | A1* | 12/2021 | Brockschmidt, Jr. .. H05B 45/10 |
| 2022/0016281 | A1 | 1/2022 | Eigner |

FOREIGN PATENT DOCUMENTS

| | | |
|---|---|---|
| EP | 3915596 | 12/2021 |
| WO | WO 2016/064441 | 4/2016 |
| WO | WO 2019/241453 | 12/2019 |

OTHER PUBLICATIONS

U.S. Appl. No. 17/016,466, filed Sep. 10, 2020.
U.S. Appl. No. 29/735,235, filed May 19, 2020.
U.S. Appl. No. 17/039,011, filed Sep. 30, 2020.
U.S. Appl. No. 17/026,414, filed Sep. 21, 2020.
U.S. Appl. No. 17/020,942, filed Sep. 15, 2020.
U.S. Appl. No. 16/987,514, filed Aug. 7, 2020.
U.S. Appl. No. 17/104,628, filed Nov. 25, 2020.
U.S. Appl. No. 16/987,647, filed Aug. 7, 2020.
U.S. Appl. No. 17/026,417, filed Sep. 21, 2020.
"Honeywell UV Treatment System," https://aerospace.honeywell.com/en/learn/products/cabin/uv-cabin-system.
U.S. Appl. No. 17/026,435, filed Sep. 21, 2020.
U.S. Appl. No. 17/022,392, filed Sep. 16, 2020.

* cited by examiner

SYSTEMS AND METHODS OF VERIFYING EFFECTIVE MOTION OF A WAND ASSEMBLY OF AN ULTRAVIOLET (UV) LIGHT SANITIZING SYSTEM

RELATED APPLICATIONS

This application relates to and claims priority benefits from U.S. Provisional Patent Application No. 63/055,389, entitled "Systems and Methods of Verifying Effective Motion of a Wand Assembly of an Ultraviolet (UV) Light Sanitizing System," filed Jul. 23, 2020.

FIELD OF THE DISCLOSURE

Embodiments of the subject disclosure generally relate to sanitizing systems, and more particularly to systems and methods of verifying that motion of a wand assembly of a sanitizing system is sufficient to sanitize a surface of a component.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light. In order to sanitize a surface of a structure, a known UV light sterilization method emits a broad spectrum UVC light onto the structure.

Portable sanitizing systems having wand assemblies are being developed to sanitize components. A wand assembly of a portable sanitizing system includes a UV lamp that is configured to emit UV light. Typically, an operator moves the wand assembly over a surface of a component to sanitize the surface. However, the individual typically does not know if the wand assembly is being moved too fast or too slow to effectively and efficiently sanitize the surface.

In general, manual processes for disinfecting surfaces using handheld devices have varying degrees of consistency.

SUMMARY OF THE DISCLOSURE

A need exists for a system and a method to verify that motion of a wand assembly having a UV lamp is sufficient to sanitize a surface of a component. Further, a need exists for a system and a method to ensure the correct dosage of UV light is delivered to a surface to effectively sanitize the surface.

With those needs in mind, certain embodiments of the subject disclosure provide a system including a wand assembly including a sanitizing head having an ultraviolet (UV) lamp configured to emit UV light to sanitize a surface of a component. The wand assembly further includes a first monitored member. The system also includes a second monitored member. A verification control unit is in communication with one or both of the first monitored member or the second monitored member. The verification control unit is configured to detect a speed of the wand assembly based on a comparison of the first monitored member in relation to the second monitored member.

In at least one example, the verification control unit determines whether or not the speed of the wand assembly is sufficient to sanitize the surface based on a comparison of the speed of the wand assembly and pacing data stored in memory. The verification control unit outputs an alert signal in response to the speed being outside of a defined range as set forth in the pacing data. The verification control unit outputs a proper speed signal in response to the speed being within the define range as set forth in the pacing data.

In at least one embodiment, the wand assembly further includes an indicator that is configured to indicate a status of the speed of the wand assembly. For example, the indicator includes one or both of at least one light or a speaker. As another example, the indicator includes a screen that shows text regarding the speed.

In at least one embodiment, the second monitored member is secured to a fixed structure within an internal cabin of a vehicle. In at least one other embodiment, the second monitored member is secured to a portion of a backpack assembly that is coupled to the wand assembly.

In at least one embodiment, one of the wand assembly, a backpack assembly, or a case assembly includes the verification control unit.

In at least one embodiment, the verification control unit compares the speed of the wand assembly at a range from the surface in relation to pacing data stored in the memory to determine whether or not the speed of the wand assembly is sufficient to sanitize the surface.

In at least one embodiment, one of the first monitored member or the second monitored member is a radio frequency (RF) receiver, and the other of the first monitored member or the second monitored member is an RF emitter.

In at least one other embodiment, one of the first monitored member or the second monitored member is a camera, and the other of the first monitored member or the second monitored member is an optical target.

In at least one other embodiment, one of the first monitored member or the second monitored member is an infrared source, and the other of the first monitored member or the second monitored member is an infrared optical target.

In at least one other embodiment, one of the first monitored member or the second monitored member is a LIDAR detector, and the other of the first monitored member or the second monitored member is a LIDAR optical target.

In at least one other embodiment, the first monitored member is an accelerometer.

In at least one embodiment, the UV lamp is configured to emit the UV light within a far UV spectrum. For example, the UV lamp is configured to emit the UV light at a wavelength of 222 nm.

In at least one other embodiment, the UV lamp is configured to emit the UV light within a UVC spectrum. For example, the UV lamp is configured to emit the UV light at a wavelength of 254 nm.

Certain embodiments of the subject disclosure provide a method including employing a wand assembly including a sanitizing head having an ultraviolet (UV) lamp configured to emit UV light to sanitize a surface of a component, the wand assembly further including a first monitored member; communicatively coupling a verification control unit with the first monitored member and a second monitored member; and detecting, by the verification control unit, a speed of the wand assembly based on a comparison of the first monitored member in relation to the second monitored member.

In at least one embodiment, the method further includes determining, by the verification control unit, whether or not the speed of the wand assembly is sufficient to sanitize the surface based on a comparison of the speed of the wand assembly and pacing data stored in memory. In at least one embodiment, the method further includes outputting, by the verification control unit, an alert signal in response to the speed being outside of a defined range as set forth in the pacing data. In at least one embodiment, the method further includes outputting, by the verification control unit, a proper speed signal in response to the speed being within the define range as set forth in the pacing data.

In at least one embodiment, the method further includes indicating, by an indicator of the wand assembly, a status of the speed of the wand assembly.

In at least one embodiment, the method further includes securing the second monitored member to a fixed structure within an internal cabin of a vehicle.

In at least one embodiment, the method further includes securing the second monitored member to a portion of a backpack assembly that is coupled to the wand assembly.

In at least one embodiment, the method further includes comparing, by the verification control unit, the speed of the wand assembly at a range from the surface in relation to pacing data stored in the memory to determine whether or not the speed of the wand assembly is sufficient to sanitize the surface.

The features, functions, and advantages that have been discussed above in the Summary can be achieved independently in various embodiments or may be combined in yet other embodiments further details of which can be seen with reference to the following description and drawings.

Certain embodiments of the subject disclosure provide a system including a first monitored member configured to be coupled to a wand assembly that includes a sanitizing head having an ultraviolet (UV) lamp configured to emit UV light to sanitize a surface of a component. The system further includes a second monitored member. A verification control unit is in communication with one or both of the first monitored member or the second monitored member. The verification control unit is configured to detect a speed of the wand assembly based on a comparison of the first monitored member in relation to the second monitored member.

DETAILED DESCRIPTION OF THE DISCLOSURE

Figure 1:
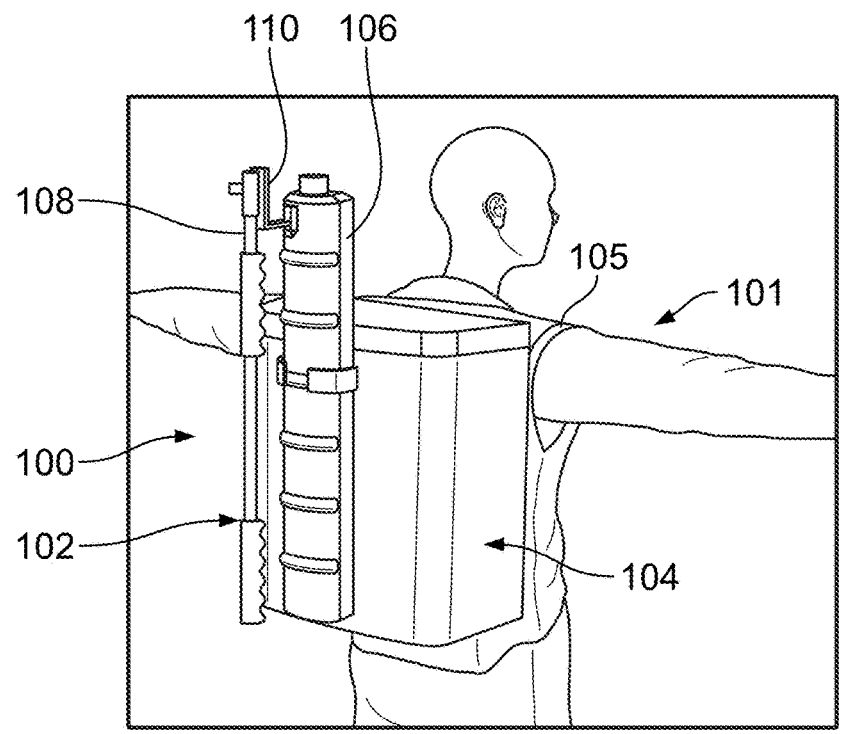
FIG. 1 illustrates a perspective view of a portable sanitizing system worn by an individual, according to an embodiment of the subject disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the subject disclosure provide a sanitizing system and method that includes an ultraviolet (UV) lamp (such as an excimer lamp) that emits UV light in a far UV light spectrum, such as at a wavelength of 222 nanometers (nm), which neutralizes (such as kills) microbes (for example, viruses and bacteria), while posing no risk to humans. In an example, the UV lamp can be used within an internal cabin to decontaminate and kill pathogens. Embodiments of the subject disclosure provide safer and more effective sanitation as compared to certain known UV systems. The UV lamp can be used in a portable sanitizing system or a fixed sanitizing system. For example, operating the UV lamp to emit sanitizing UV light having a wavelength of 222 nm can be used with a portable system or a fixed system. In at least one other embodiment, the UV lamp emits UV light having a wavelength other than within the far UV light spectrum. For example, the UV lamp can be configured to emit UV light within the UVC spectrum, such as at a wavelength of 254 nm.

Certain embodiments of the subject disclosure provide a system to verify the speed of a wand assembly to ensure that a correct dosage of sanitizing light is delivered to a surface. The system includes a radio frequency (RF) receiver located in a fixed position, such as on a location on an operator or in a fixed location in an environment (such as within an internal cabin of a vehicle). An RF emitter is disposed on the wand assembly, such as on a sanitizing head of a wand assembly. A verification control unit (such as one or more processors) is located in a backpack or case of a portable sanitizing system. A memory is in communication with or otherwise part of the processor. A speed of the wand assembly is determined by integrating the location of the sanitizing head relative to the fixed location. The operator is informed of the actual wand speed by the indicator activity, which can include a pacing light or an audio tone on the wand assembly.

Alternatively, the system can include a camera in the fixed location and an optical target on the wand. As another option, an infrared source can be on the fixed location and an infrared optical target located on the wand assembly. As another option, a light detection and ranging (LIDAR) detector can be at the fixed location and a LIDAR optical target on the wand assembly. As another option, an accelerometer can be placed on the wand assembly.

In at least one embodiment, speed at which the wand assembly is to be moved is determined by the range to the surface for a wand of a certain lamp power. Once the operator selects the range (for example, 4 inches from the surface to disinfect), the system determines the required speed to achieve the correct dosage of UV light.

In at least one embodiment, a predetermined dosage of UV light is determined by lamp power, range to target, and time of exposure. The speed of the wand assembly motion determines the time of exposure.

Wand assembly location relative to a fixed point (such as on an operator) can be determined using one or more of the following: RF emitter triangulation using an RF emitter in the wand and a receiver located in the backpack, chest harness, or other wearable device of the wand operator; RF emitter triangulation using an RF emitter located in the backpack, chest harness or other wearable device of the wand operator and an RF receiver in the wand assembly; optical triangulation by a camera located in the chest harness (or other wearable device) of the wand operator and an optical target visible on the wand; optical triangulation using a solid state LIDAR located in the chest harness (or other wearable device) of the wand operator and an LIDAR optical target visible on the wand assembly; and/or optical triangulation using a solid state infrared source located in the chest harness (or other wearable device) of the wand operator and an infrared optical reflector visible on the wand.

The sanitizing head location relative to a fixed point in a vehicle or building can be determined using RF emitter triangulation using an RF receiver in the wand assembly and emitters in fixed locations in the vehicle or building. The sanitizing head speed can be determined directly via integration of acceleration within the sanitizing head using an accelerometer on the sanitizing head.

The operator can be informed of the actual speed of the wand assembly relative to the desired speed using one or more of the following: a pacing light on the wand assembly that illuminates in different colors and blinking rates depending on whether or not the speed is correct, too fast, or too slow; and/or an audio tone that changes sound and pulse rates depending up whether they are at the correct speed, too fast, or too slow.

FIG. 1 illustrates a perspective view of a portable sanitizing system 100 worn by an individual 101, according to an embodiment of the subject disclosure. The portable sanitizing system 100 includes a wand assembly 102 coupled to a backpack assembly 104 that is removably secured to the individual through a harness 105. The wand assembly 102 includes a sanitizing head 106 coupled to a handle 108. In at least one embodiment, the sanitizing head 106 is moveably coupled to the handle 108 through a coupler 110.

In at least one other embodiment, the portable sanitizing system 100 may not be worn by the individual 101. For example, the portable sanitizing system 100 can include a case assembly that is configured to be opened and closed. The case assembly can store the wand assembly 102 when not in use. The case assembly can be opened to allow the wand assembly 102 to be removed and operated.

As shown in FIG. 1, the wand assembly 102 is in a stowed position. In the stowed position, the wand assembly 102 is removably secured to a portion of the backpack assembly 104, such as through one or more tracks, clips, latches, belts, ties, and/or the like.

In at least one other embodiment, the wand assembly 102 is stored within a case assembly in a stowed position. For example, the wand assembly 102 in the stowed position is contained within a closed case assembly. The case assembly can be opened to allow the wand assembly 102 to be removed and deployed.

Figure 2:
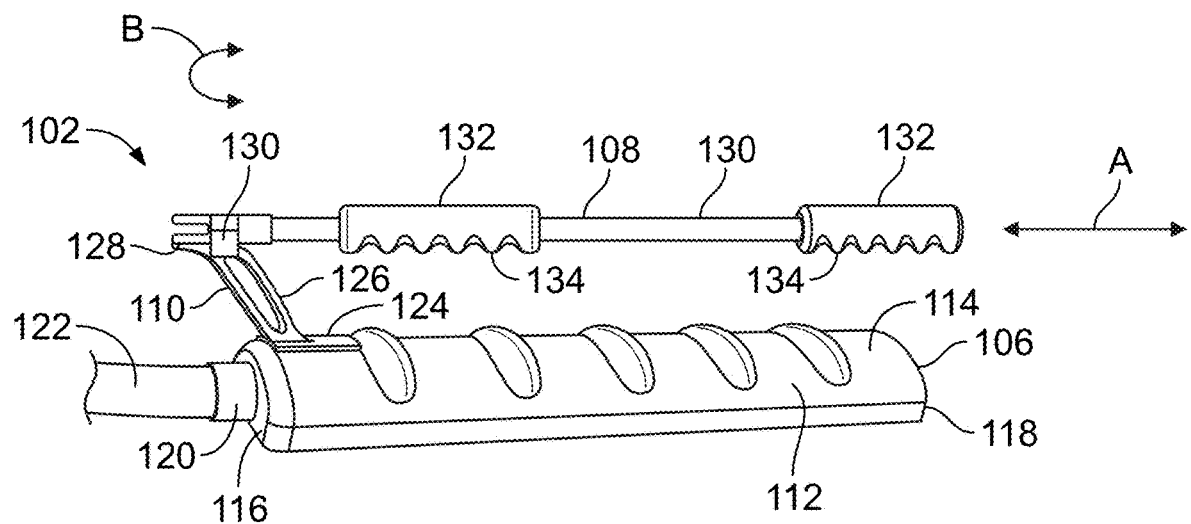
FIG. 2 illustrates a perspective lateral top view of a wand assembly, according to an embodiment of the subject disclosure.

FIG. 2 illustrates a perspective lateral top view of the wand assembly 102, according to an embodiment of the subject disclosure. The sanitizing head 106 couples to the handle 108 through the coupler 110. The sanitizing head 106 includes a shroud 112 having an outer cover 114 that extends from a proximal end 116 to a distal end 118. As described herein, the shroud 112 contains a UV lamp.

Optionally, the wand assembly 102 can include the sanitizing head 106 connected to a fixed handle. Further, the wand assembly 102 can be sized and shaped differently than shown.

A port 120 extends from the proximal end 116. The port 120 couples to a hose 122, which, in turn, couples to the backpack assembly 104 (shown in FIG. 1). The hose 122 contains electrical cords, cables, wiring, or the like that couples a power source or supply (such as one or more batteries) within the backpack assembly 104 (shown in FIG. 1) to a UV lamp 140 within the shroud 112. Optionally, the electrical cords, cables, wiring, or the like can be outside of the hose 122. In at least one embodiment, the hose 122 also contains an air delivery line, such as an air tube) that fluidly couples an internal chamber of the shroud 112 to an air blower, vacuum generator, air filters, and/or the like within the backpack assembly 104.

The coupler 110 is secured to the outer cover 114 of the shroud 112, such as proximate to the proximal end 116. The coupler 110 can include a securing beam 124 secured to the outer cover 114, such as through one or more fasteners, adhesives, and/or the like. An extension beam 126 outwardly extends from the securing beam 124, thereby spacing the handle 108 from the shroud 112. A bearing assembly 128 extends from the extension beam 126 opposite from the securing beam 124. The bearing assembly 128 includes one or more bearings, tracks, and/or the like, which allow the handle 108 to linearly translate relative to the coupler 110 in the directions of arrows A, and/or pivot about a pivot axle in the directions of arc B. Optionally, the securing beam 124 can include a bearing assembly that allows the sanitizing head 106 to translate in the directions of arrows A, and/or rotate (for example, swivel) in the directions of arc B in addition to, or in place of, the handle 108 being coupled to the bearing assembly 128 (for example, the handle 108 can be fixed to the coupler 110).

In at least one other example, the wand assembly 102 does not include the coupler 110. Instead, the handle 108 can be fixed to the shroud 112, for example.

In at least one example, the handle 108 includes a rod, pole, beam, or the like 130, which can be longer than the shroud 112. Optionally, the rod 130 can be shorter than the shroud 112. One or more grips 132 are secured to the rod 130. The grips 132 are configured to be grasped and held by an individual. The grips 132 can include ergonomic tactile features 134.

Optionally, the wand assembly 102 can be sized and shaped differently than shown. For example, the handle 108 can be fixed in relation to the shroud 112. Further, the handle 108 may not be configured to move relative to itself and/or the shroud 112. For example, the handle 108 and the shroud 112 can be integrally molded and formed as a single unit.

In at least one example, the wand assembly 102 is not coupled to a backpack assembly. For example, the wand assembly 102 is a standalone unit having a power source, such as one or more batteries. As another example, the wand assembly 102 is coupled to a case assembly.

Figure 3:
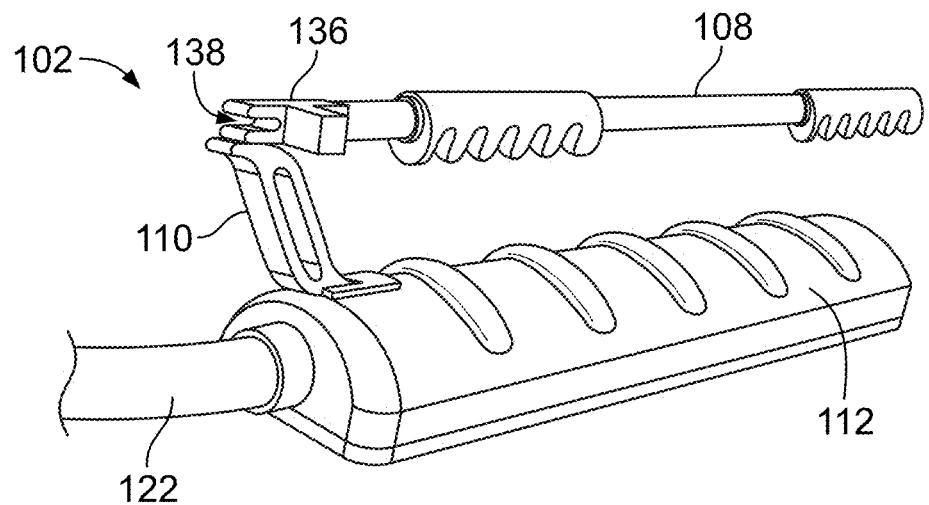
FIG. 3 illustrates a perspective rear view of the wand assembly of FIG. 2.
Figure 4:
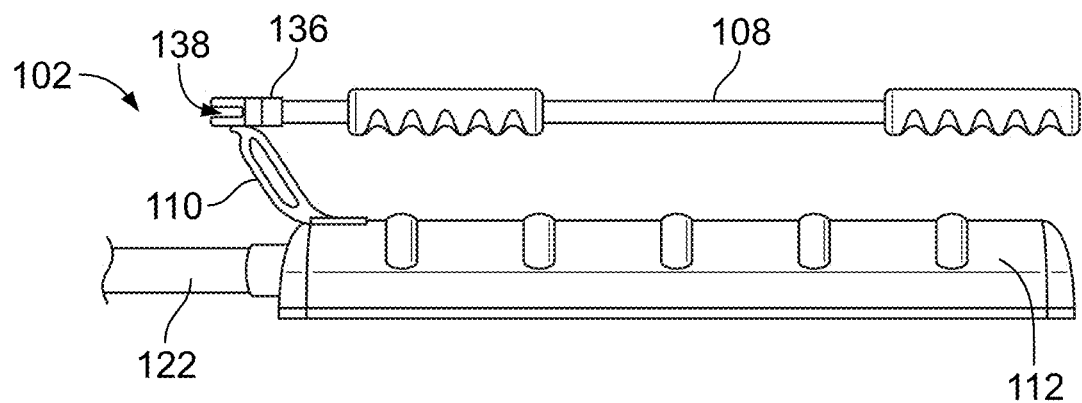
FIG. 4 illustrates a perspective lateral view of the wand assembly of FIG. 2.

FIG. 3 illustrates a perspective rear view of the wand assembly 102 of FIG. 2. FIG. 4 illustrates a perspective lateral view of the wand assembly 102 of FIG. 2. Referring to FIGS. 3 and 4, the handle 108 can pivotally couple to the coupler 110 through a bearing 136 having a pivot axle 138 that pivotally couples the handle 108 to the coupler 110. The handle 108 can further be configured to linearly translate into and out of the bearing 136. For example, the handle 108 can be configured to telescope in and out. Optionally, or alternatively, in at least one embodiment, the handle 108 can include a telescoping body that allows the handle 108 to outwardly extend and inwardly recede. In at least one other embodiment, the handle 108 may not be configured to move, extend, retract, or the like relative to the shroud 112.

Figure 5:
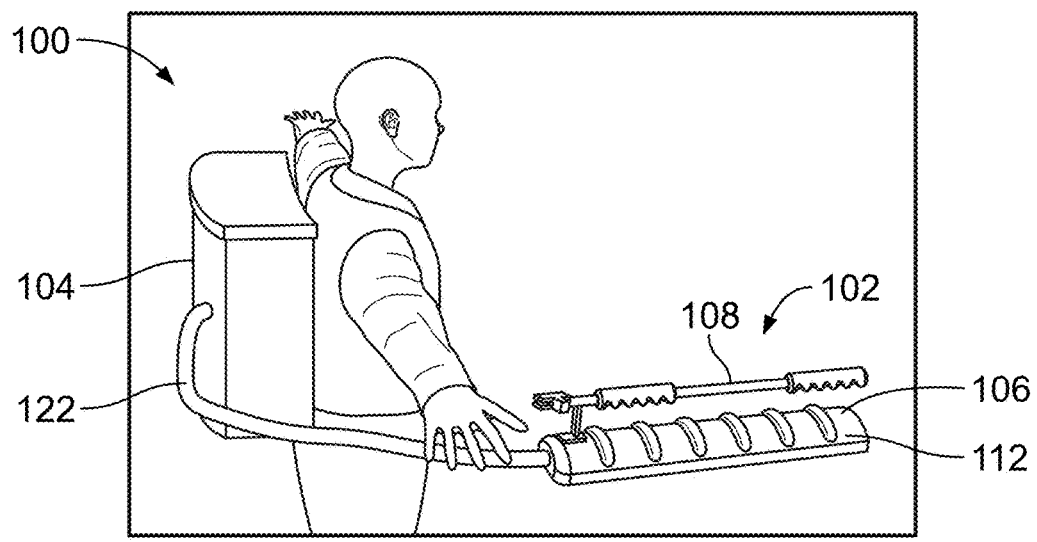
FIG. 5 illustrates a perspective view of the portable sanitizing system in a compact deployed position, according to an embodiment of the subject disclosure.

FIG. 5 illustrates a perspective view of the portable sanitizing system 100 in a compact deployed position, according to an embodiment of the subject disclosure. The wand assembly 102 is removed from the backpack assembly 104 (as shown in FIG. 1) into the compact deployed position, as shown in FIG. 5. The hose 122 connects the wand assembly 102 to the backpack assembly 104. In the compact deployed position, the sanitizing head 106 is fully retracted in relation to the handle 108.

Figure 6:
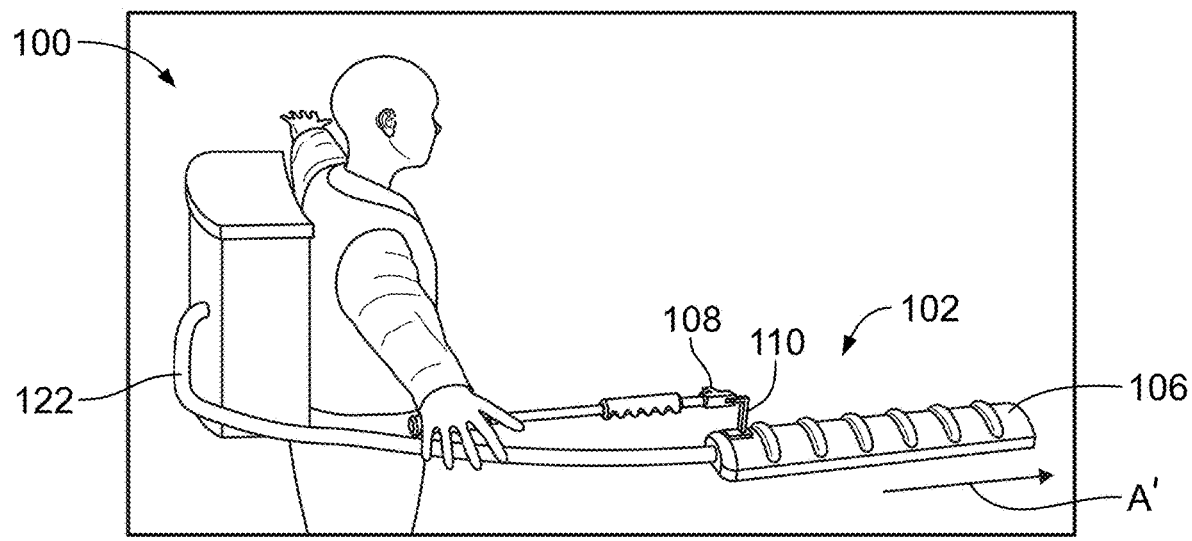
FIG. 6 illustrates a perspective view of the portable sanitizing system having a sanitizing head in an extended position, according to an embodiment of the subject disclosure.

FIG. 6 illustrates a perspective view of the portable sanitizing system 100 having the sanitizing head 106 in an extended position, according to an embodiment of the subject disclosure. In order to extend the sanitizing head 106 relative to the handle 108, the sanitizing head 106 is outwardly slid relative to the handle 108 in the direction of arrow A' (or the handle 108 is rearwardly slid relative to the sanitizing head 106). As noted, the sanitizing head 106 is able to linearly translate in the direction of arrow A' relative to the handle 108 via the coupler 110. The outward extension of the sanitizing head 106, as shown in FIG. 6, allows for the portable sanitizing system 100 to easily reach distant areas. Alternatively, the sanitizing head 106 may not linearly translate relative to the handle 108.

Figure 7:
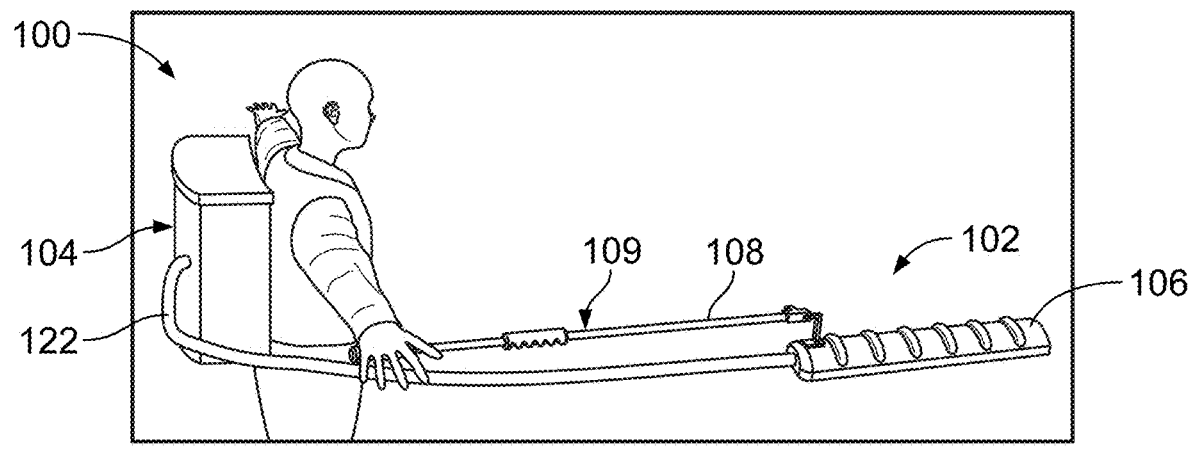
FIG. 7 illustrates a perspective view of the portable sanitizing system having the sanitizing head in an extended position and a handle in an extended position, according to an embodiment of the subject disclosure.

FIG. 7 illustrates a perspective view of the portable sanitizing system 100 having the sanitizing head 106 in an extended position and the handle 108 in an extended position, according to an embodiment of the subject disclosure. To reach even further, the handle 108 can be configured to linearly translate, such as through a telescoping portion, to allow the sanitizing head 106 to reach further outwardly. Alternatively, the handle 108 may not be configured to extend and retract.

In at least one embodiment, the handle 108 can include a lock 109. The lock 109 is configured to be selectively operated to secure the handle 108 into a desired extended (or retracted) position.

Figure 8:
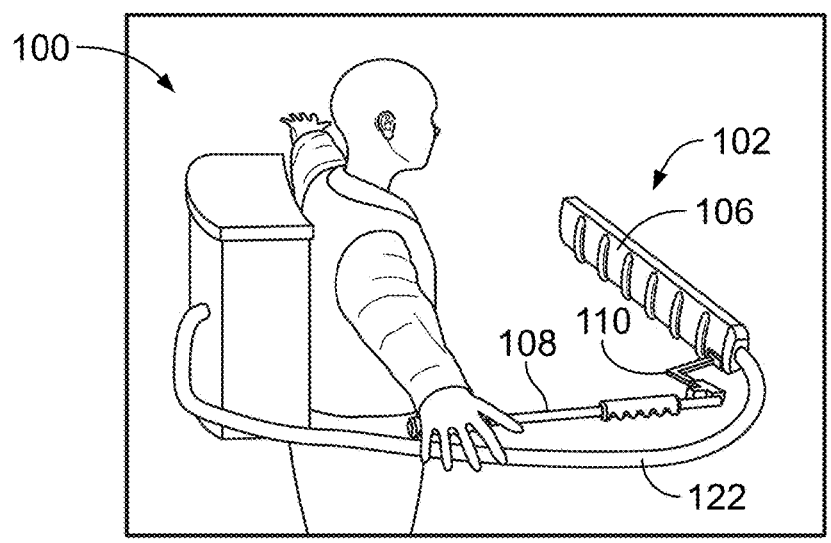
FIG. 8 illustrates a perspective view of the portable sanitizing system having the sanitizing head rotated in relation to the handle, according to an embodiment of the subject disclosure.

FIG. 8 illustrates a perspective view of the portable sanitizing system 100 having the sanitizing head 106 rotated in relation to the handle 108, according to an embodiment of the subject disclosure. As noted, the sanitizing head 106 is configured to rotate relative to the handle 108 via the coupler 110. Rotating the sanitizing head 106 relative to the handle 108 allows the sanitizing head 106 to be moved to a desired position, and sweep or otherwise reach into areas that would otherwise be difficult to reach if the sanitizing head 106 was rigidly fixed to the handle 108. Alternatively, the sanitizing head 106 may not be rotatable relative to the handle 108.

Figure 9:
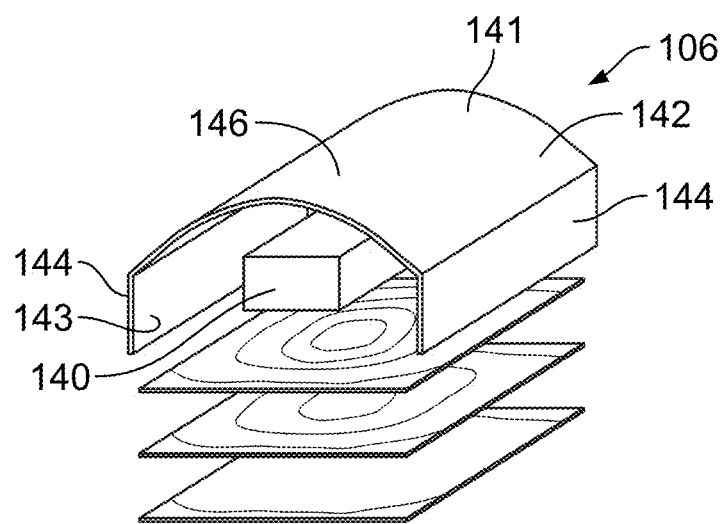
FIG. 9 illustrates a perspective end view of a UV lamp and a reflector of the sanitizing head, according to an embodiment of the subject disclosure.

FIG. 9 illustrates a perspective end view of a UV lamp 140 and a reflector 142 of the sanitizing head 106, according to an embodiment of the subject disclosure. The UV lamp 140 and the reflector 142 are secured within the shroud 112 (shown in FIG. 2, for example) of the sanitizing head 106. In at least one embodiment, the reflector 142 is secured to an underside 141 of the shroud 112, such as through one or more adhesives. As another example, the reflector 142 is an integral part of the shroud 112. For example, the reflector 142 can be or otherwise provide the underside 141 of the shroud 112. The reflector 142 provides a reflective surface 143 (such as formed of Teflon, a mirrored surface, and/or the like) that is configured to outwardly reflect UV light emitted by the UV lamp 140. In at least one example, shroud 112 can be or include a shell formed of fiberglass, and the reflector 142 can be formed of Teflon that provides a 98% reflectivity. In at least one embodiment, the reflector 142 can be a multi-piece reflector.

The reflector 142 can extend along an entire length of the underside 141 of the shroud 112. Optionally, the reflector 142 can extend along less than an entire length of the underside 141 of the shroud 112.

The UV lamp 140 can extend along an entire length (or along substantially the entire length, such as between the ends 116 and 118). The UV lamp 140 is secured to the reflector 142 and/or the shroud 112 through one or more mounts, such as brackets, for example. The UV lamp 140 includes one or more UV light emitters, such as one more bulbs, light emitting elements (such as light emitting diodes), and/or the like. In at least one embodiment, the UV lamp 140 is configured to emit UV light in the far UV spectrum, such as at a wavelength between 200 nm-230 nm. In at least one embodiment, the UV lamp 140 is configured to emit UV light having a wavelength of 222 nm. For example, the UV lamp 140 can be or include a 300 W bulb that is configured to emit UV light having a wavelength of 222 nm. Alternatively, the UV lamp 140 can be configured to emit UV light in other portions of the UV spectrum, such as the UVC spectrum (for example, having a wavelength of 254 nm).

As shown, the reflector 142 includes flat, upright side walls 144 connected together through an upper curved wall 146. The upper curved wall 146 can be bowed outwardly away from the UV lamp 140. For example, the upper curved wall 146 can have a parabolic cross-section and/or profile.

It has been found that the straight, linear side walls 144 provide desired reflection and/or focusing of UV light emitted from the UV lamp 140 toward and onto a desired location. Alternatively, the side walls 144 may not be linear and flat.

Figure 10:
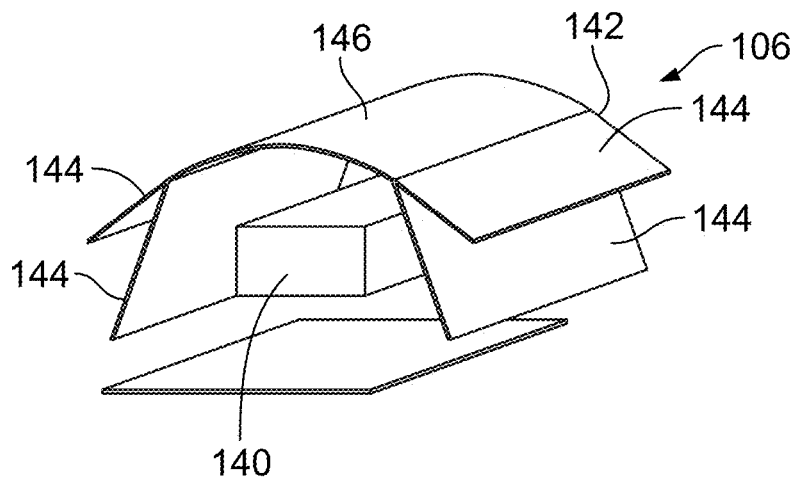
FIG. 10 illustrates a perspective end view of a UV lamp and a reflector of the sanitizing head, according to an embodiment of the subject disclosure.

FIG. 10 illustrates a perspective end view of the UV lamp 140 and a reflector 142 of the sanitizing head, according to an embodiment of the subject disclosure. The reflector 142 shown in FIG. 10 is similar to the reflector 142 shown in FIG. 9, except that the side walls 144 can outwardly angle from the upper curved wall 146.

Figure 11:
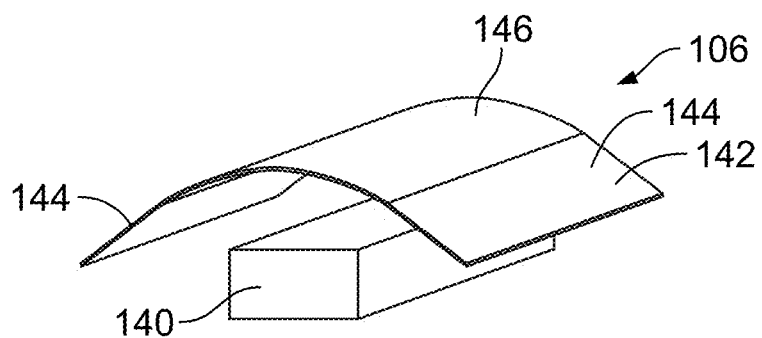
FIG. 11 illustrates a perspective end view of a UV lamp and a reflector of the sanitizing head, according to an embodiment of the subject disclosure.

FIG. 11 illustrates a perspective end view of the UV lamp 140 and the reflector 142 of the sanitizing head, according to an embodiment of the subject disclosure. In this embodiment, the side walls 144 can be curved according to the curvature of the upper curved wall 146.

Figure 12:
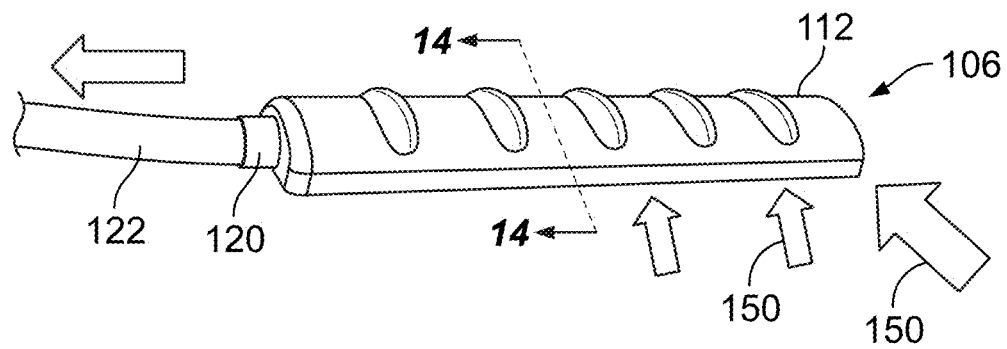
FIG. 12 illustrates a perspective top view of the sanitizing head.
Figure 13:
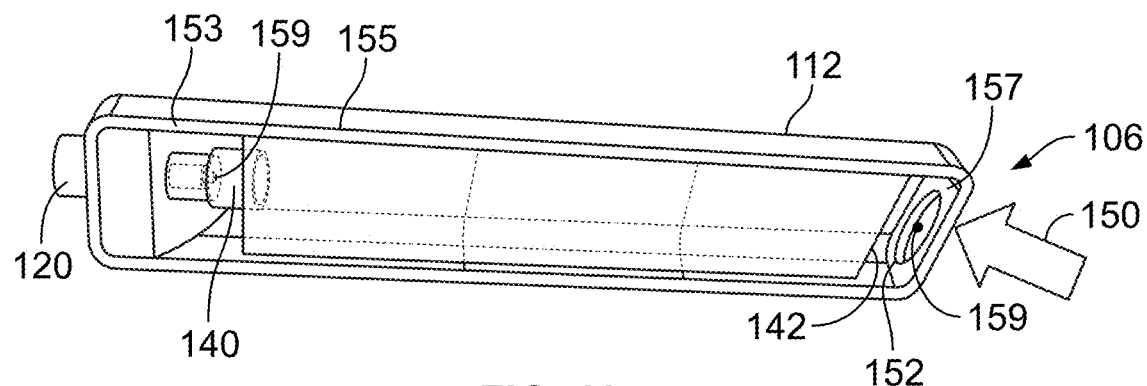
FIG. 13 illustrates a perspective bottom view of the sanitizing head.
Figure 14:
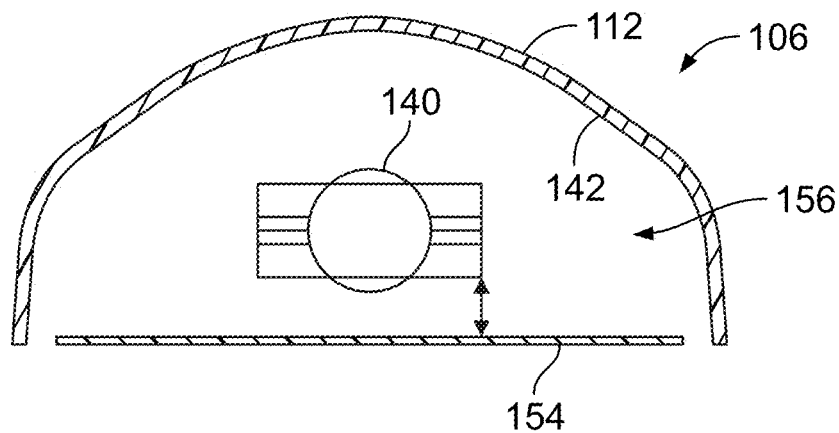
FIG. 14 illustrates an axial cross-sectional view of the sanitizing head through line 14-14 of FIG. 12.

FIG. 12 illustrates a perspective top view of the sanitizing head 106. FIG. 13 illustrates a perspective bottom view of the sanitizing head 106. FIG. 14 illustrates an axial cross-sectional view of the sanitizing head 106 through line 14-14 of FIG. 12. Referring to FIGS. 12-14, air 150 is configured to be drawn into the sanitizing head 106 through one or more openings 152 (or simply an open chamber) of the shroud 112. The air 150 is drawn into the sanitizing head 106, such as via a vacuum generator within the backpack assembly 104 (shown in FIG. 1). The air 150 is drawn into the shroud 112, and cools the UV lamp 140 as it passes over and around the UV lamp 140. The air 150 passes into the port 120 and into the hose 122, such as within an air tube within the hose 122. The air 150 not only cools the UV lamp 140, but also removes ozone, which can be generated by operation of the UV lamp 140, within the shroud 112. The air 150 can be drawn to an air filter, such as an activated carbon filter, within the backpack assembly 104.

In at least one embodiment, the portable sanitizing system 100 can also include an alternative ozone mitigation system. As an example, the ozone mitigation system can be disposed in the shroud 112 or another portion of the system, and may include an inert gas bath, or a face inert gas system, such as in U.S. Pat. No. 10,232,954.

Referring to FIG. 13, in particular, a bumper 153 can be secured to an exposed lower circumferential edge 155 of the shroud 112. The bumper 153 can be formed of a resilient material, such as rubber, another elastomeric material, open or closed cell foam, and/or the like. The bumper 153 protects the sanitizing head 106 from damage in case the sanitizing head 106 inadvertently contacts a surface. The bumper 153 also protects the surface from damage.

The openings 152 can be spaced around the lower surface of the shroud 112 such that they do not provide a direct view of the UV lamp 140. For example, the openings 152 can be positioned underneath portions that are spaced apart from the UV lamp 140.

Referring to FIG. 14, in particular, the sanitizing head 106 can include a cover plate 154 below the UV lamp 140. The cover plate 154 may be formed of glass, for example, and can be configured to filter UV light emitted by the UV lamp 140. The UV lamp 140 can be secured within an interior chamber 156 defined between the reflector 142 and the cover plate 154. In at least one embodiment, the cover plate 154 is or otherwise includes a far UV band pass filter. For example, the cover plate 154 can be a 222 nm band pass filter that filters UV light emitted by the UV lamp 140 to a 222 nm wavelength. As such, UV light that is emitted from the sanitizing head 106 can be emitted at a wavelength of 222 nm. In at least one other embodiment, the cover plate 154 can be a 254 nm band pass filter that filter UV light emitted by the UV lamp 140 to a 254 nm wavelength. As such, UV light that is emitted from the sanitizing head can be emitted at a wavelength of 254 nm.

Referring to FIGS. 13 and 14, a rim 157 (such as a 0.020" thick Titanium rim) can connect the cover plate 154 to the shroud 112. The rim 157 can distribute impact loads therethrough and/or therearound.

In at least one embodiment, ranging light emitting diodes (LEDs) 159 can be disposed proximate to ends of the UV lamp 140. The ranging LEDs 159 can be used to determine a desired range to a structure that is to be sanitized, for example. In at least one embodiment, the ranging LEDs 159 can be disposed on or within the rim 157 and/or the cover plate 154. As another example, the sanitizing head 106 can be configured for range guidance, as disclosed in U.S. Provisional Application No. 63/027,869, which was filed May 20, 2020, which is hereby incorporated by reference in its entirety.

Figure 15:
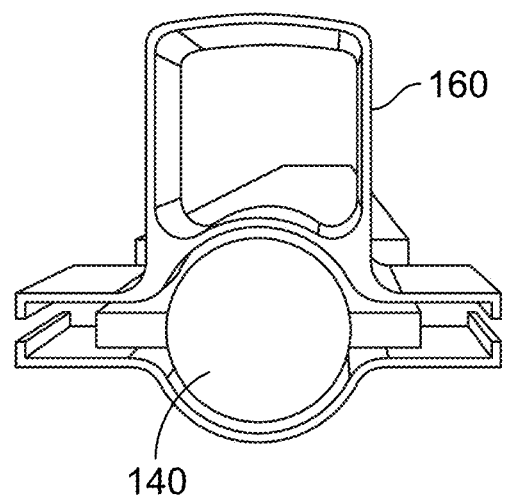
FIG. 15 illustrates a perspective end view of the UV lamp secured to a mounting bracket, according to an embodiment of the subject disclosure.

FIG. 15 illustrates a perspective end view of the UV lamp 140 secured to a mounting bracket or clamp 160, according to an embodiment of the subject disclosure. Each end of the UV lamp 140 can be coupled to mounting bracket or clamp 160, which secures the UV lamp 140 to the shroud 112 (shown in FIGS. 12-14). A buffer, such as a thin (for example, 0.040") sheet of silicon can be disposed between the end of the UV lamp 140 and the bracket 160. Optionally, the UV lamp 140 may be secured to the shroud 112 through brackets or clamps that differ in size and shape than shown. As another example, the UV lamp 140 can be secured to the shroud 112 through adhesives, fasteners, and/or the like.

Figure 16:
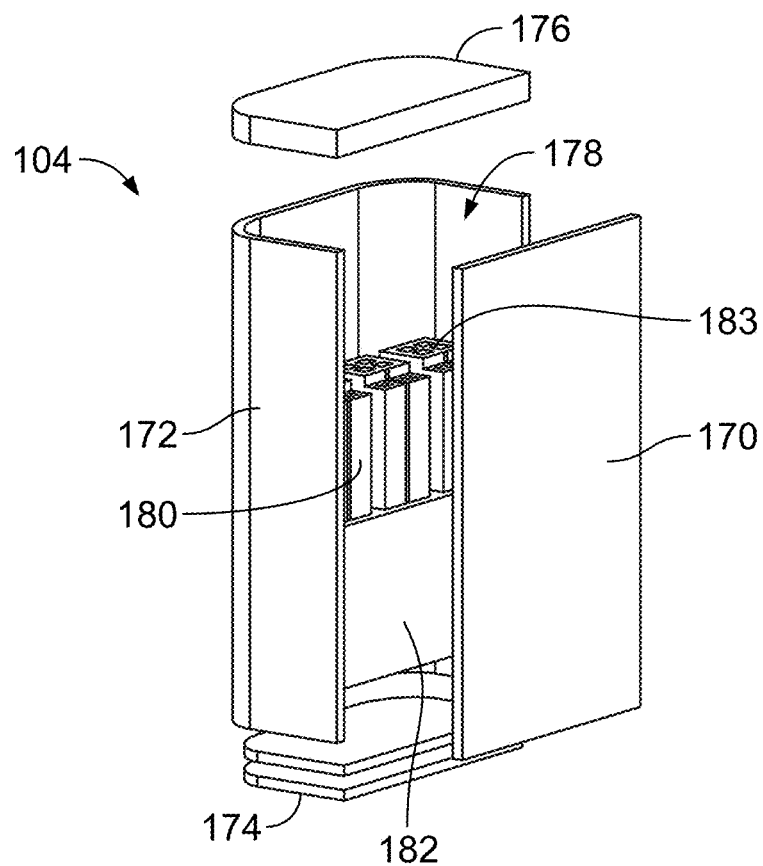
FIG. 16 illustrates a perspective exploded view of a backpack assembly, according to an embodiment of the subject disclosure.

FIG. 16 illustrates a perspective exploded view of the backpack assembly 104, according to an embodiment of the subject disclosure. The backpack assembly 104 includes a front wall 170 that couples to a rear shell 172, a base 174, and a top wall 176. An internal chamber 178 is defined between the front wall 170, the rear shell 172, the base 174, and the top wall 176. One or more batteries 180, such as rechargeable Lithium batteries, are contained within the internal chamber 178. An air generation sub-system 182 is also contained within the internal chamber 178. The air generation sub-system 182 is in fluid communication with an air tube within the hose 122 (shown in FIG. 2, for example). The air generation sub-system 182 can include an airflow device, such as a vacuum generator, an air blower, and/or the like. The airflow device is configured to generate airflow to cool the UV lamp, draw air from the sanitizing head 106 into the backpack assembly 104 and out through an exhaust, draw or otherwise remove generated ozone away from the shroud 112, and/or the like.

One or more air filters 183, such as carbon filters, are within the backpack assembly 104. The air filters 183 are in communication with the air tube or other such delivery duct or line that routes air through the hose 122 and into the backpack assembly 104. The air filters 183 are configured to filter the air that is drawn into the backpack assembly 104 from the shroud 112. For example, the air filters 183 can be configured to remove, deactivate, or otherwise neutralize ozone.

The batteries 180 and/or a power supply within the backpack assembly 104 provides operating power for the UV lamp 140 of the sanitizing head 106 (shown in FIG. 2, for example). The top wall 176 (for example, top cap) can be removably coupled to the front wall 170 and the rear shell 172. The top wall 176 can be removed to provide access to the batteries 180 (such as to remove and/or recharge the batteries), for example. Additional space can be provided within the backpack assembly 104 for storage of supplies, additional batteries, additional components, and/or the like. In at least one embodiment, the front wall 170, the rear shell 172, the base 174, and the top wall 176 can be formed of fiberglass epoxy.

Figure 17:
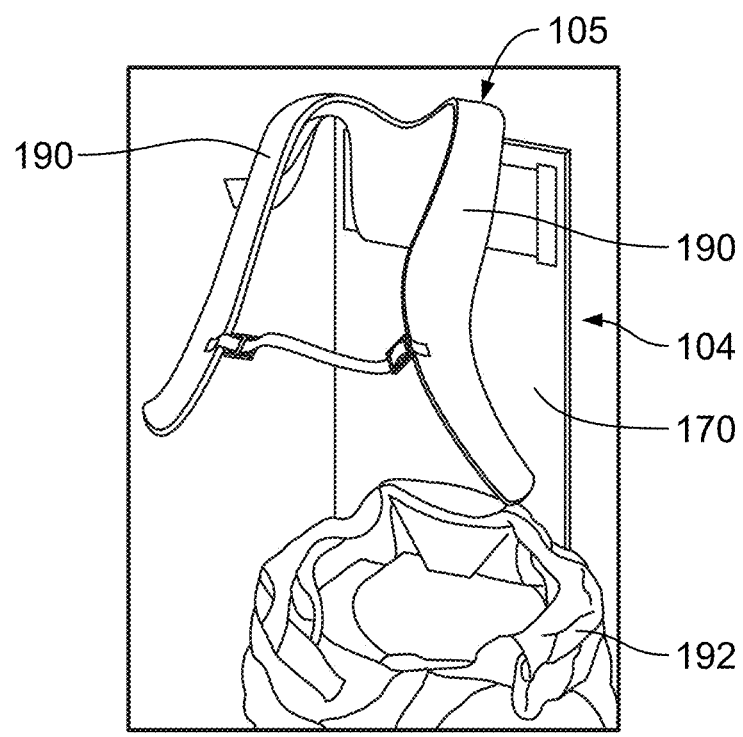
FIG. 17 illustrates a perspective front view of a harness coupled to a backpack assembly, according to an embodiment of the subject disclosure.

FIG. 17 illustrates a perspective front view of the harness 105 coupled to the backpack assembly 104, according to an embodiment of the subject disclosure. The harness 105 can include shoulder straps 190 and/or a waist or hip belt or strap 192, which allow the individual to comfortably wear the backpack assembly 104.

Referring to FIGS. 1-17, in operation, the individual can walk through an area wearing the backpack assembly 104. When a structure to be sanitized is found, the individual can position grasp the handle 108 and position the sanitizing head 106 as desired, such as by extending and/or rotating the sanitizing head 106 relative to the handle 108. The individual can then engage an activation button on the handle 108, for example, to activate the UV lamp 140 to emit sanitizing UV light onto the structure. As the UV lamp 140 is activated, air 150 is drawn into the shroud 112 to cool the UV lamp 140, and divert any generated ozone into the backpack assembly 104, where it is filtered by the air filters 183.

The extendable wand assembly 102 allows the sanitizing head 106 to reach distant areas, such as over an entire set of three passenger seats, from a row within an internal cabin of a commercial aircraft.

Figure 18:
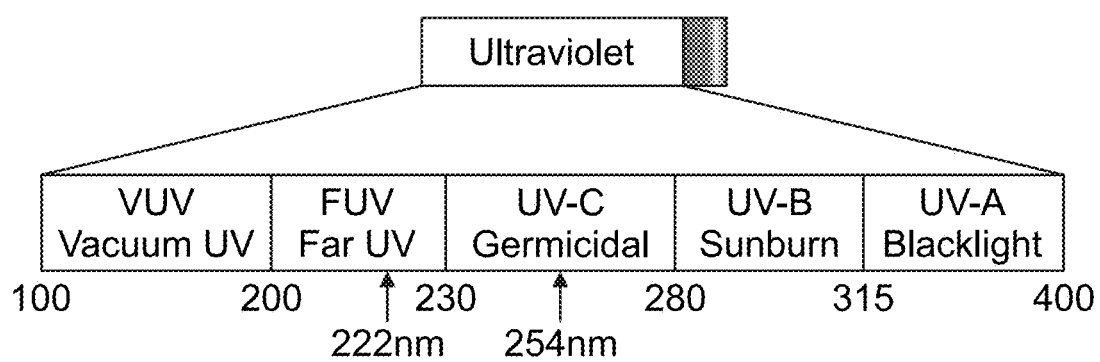
FIG. 18 illustrates an ultraviolet light spectrum.

FIG. 18 illustrates an ultraviolet light spectrum. Referring to FIGS. 1-18, in at least one embodiment, the sanitizing head 106 is configured to emit sanitizing UV light (through operation of the UV lamp 140) within a far UV spectrum, such as between 200 nm to 230 nm, and/or a UVC spectrum. In at least one embodiment, the sanitizing head 106 emits sanitizing UV light having a wavelength of 222 nm. In at least one other embodiment, the sanitizing head 106 emits sanitizing UV light having a wavelength of 254 nm.

Figure 19:
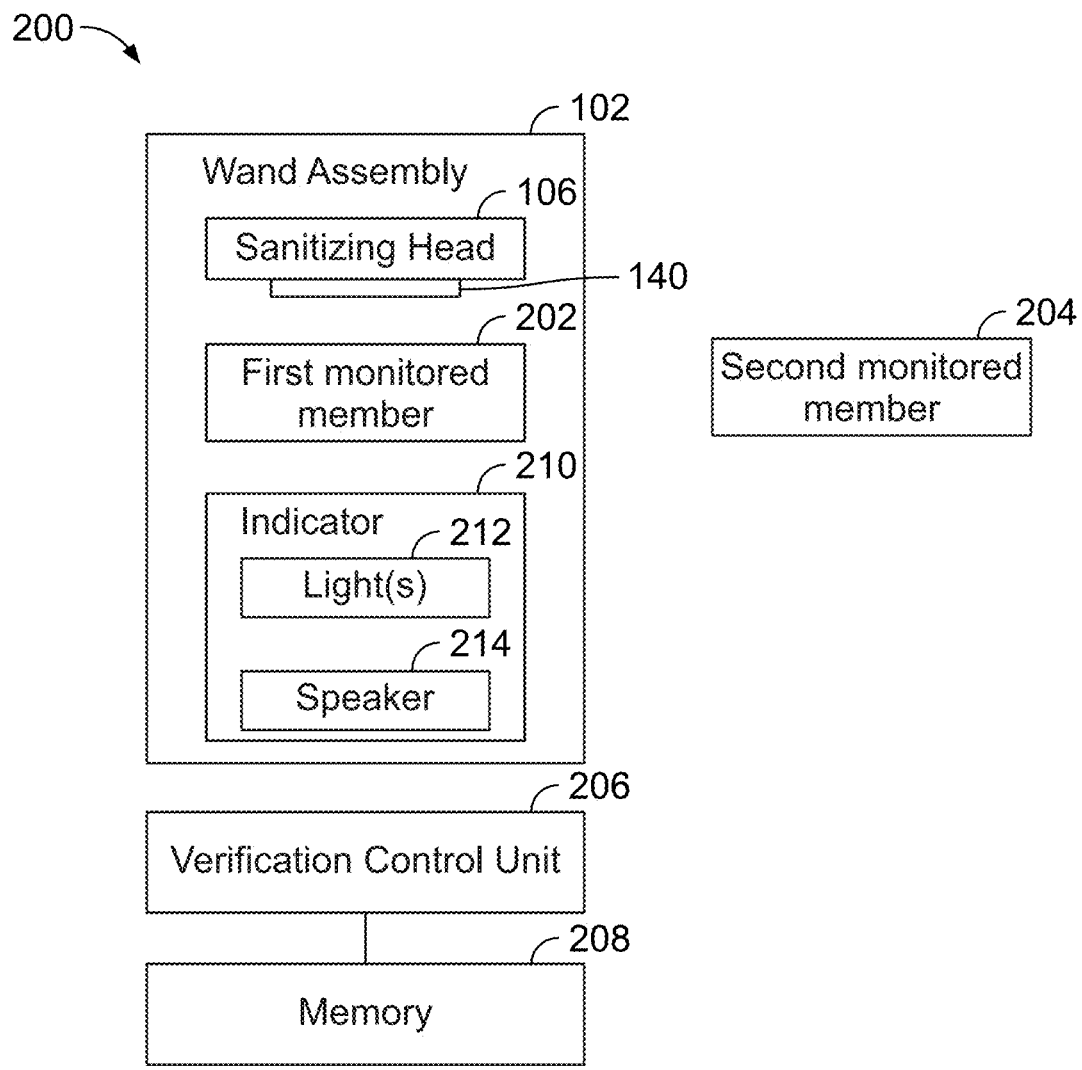
FIG. 19 illustrates a schematic block diagram of a wand speed verification system, according to an embodiment of the subject disclosure.

FIG. 19 illustrates a schematic block diagram of a wand speed verification system 200, according to an embodiment of the subject disclosure. The wand speed verification system 200 includes the wand assembly 102 having the sanitizing head 106. In at least one embodiment, a first monitored member 202 is part of or secured to the wand assembly 102.

A second monitored member 204 is separate and distinct from the wand assembly 102. The second monitored member 204 can be secured to a fixed structure, such as within an internal cabin of a vehicle. Optionally, the second monitored member 204 can be secured to (such as on or in) the backpack assembly 104 (shown in FIG. 1), a case assembly, a wearable device worn by the operator, or the like.

A verification control unit 206 is in communication with a memory 208, such as through one or more wired or wireless connections. The memory 208 can be part of the verification control unit 206 or can be separate and distinct therefrom. In at least one embodiment, the verification control unit 206 and the memory 208 are within the backpack assembly 104, a case assembly, or the wand assembly 102. In at least one other embodiment, the verification control unit 206 and the memory 208 are remote from the backpack assembly 104, a case assembly, the wand assembly 102, and the like. For example, the verification control unit 206 and the memory 208 can be within a portion of an internal cabin of a vehicle.

The verification control unit 206 is in communication with the first monitored member 202 and/or the second monitored member 204, such as via one or more wired or wireless signals. The verification control unit 206 receives signals output from the first monitored member 202 and/or the second monitored member 204 to determine a speed of movement of the sanitizing head 106, for example.

In at least one embodiment, the wand assembly 102 includes an indicator 210, such as on a portion of the wand assembly 102 (for example, the sanitizing head 106 or a handle connected to the sanitizing head 106). The indicator 210 includes one or more lights 212, and/or a speaker 214. As another example, the indicator 210 includes a screen that displays text, graphics, or video. As another example, the indicator 210 can be a vibrating device that is configured to provide feedback through vibrations.

In operation, the memory 208 stores pacing data for the wand assembly 102. For example, the pacing data includes a pacing speed of motion of the sanitizing head 106 for various ranges from a surface to be sanitized, a power of the UV lamp 140, the particular wavelength of UV light emitted, a time for effective dosage, and the like.

The wand assembly 102 is operated by moving the sanitizing head 106 over a surface to be disinfected. The range of the sanitizing head 106 from the surface is detected by one or more sensors, such as disclosed in U.S. Provisional Application No. 63/027,869. The sensors are in communication with the verification control unit 206. As such, the verification control unit 206 determines the range of the sanitizing head 106 from the surface based on signals output from the sensors.

As the sanitizing head 106 is moved, the first monitored member 202 moves in relation to the second monitored member 204. The verification control unit 206 detects the motion from the signal(s) output by one or both of the first monitored member 202 and/or the second monitored member 204. In this manner, the verification control unit 206 determines the speed of motion of the wand assembly 102 in relation to the surface.

The verification control unit 206 then compares the detected speed of the wand assembly 102, the range of the wand assembly 102 from the surface, the type of UV light emitted, and the power of the UV light emitted with the pacing data stored in the memory 208. The pacing data indicates the correct speed for proper sanitization of the surface at the detected range, for the particular UV light and emitted power of UV light. Based on the comparison of the detected speed with the pacing data, the verification control unit 206 determines whether the actual speed of the wand assembly 102, as detected from the signal(s) received from one or both of the first monitored member 202 and/or the second monitored member 204, is sufficient to sanitize the surface. If the actual speed of the wand assembly 102 is correct (for example, determined to be equal to the correct speed or within an acceptable range corresponding to the correct speed), the verification control unit 206 outputs an indication signal to the wand assembly 102 indicating a correct speed. The indicator 210 can indicate the correct speed through corresponding light energy (such as a green light) as emitted by the light(s) 212, and/or an audio signal emitted through the speaker 214. As another example, the indicator 210 includes a screen that displays text, graphics, or video regarding the speed of the wand assembly 102.

If, however, the actual speed of the wand assembly is too fast, thereby providing insufficient sanitization (for example, determined to be greater than the correct speed to not within the acceptable range corresponding to the correct speed), the verification control unit 206 outputs an indication signal to the wand assembly 102 indicating that the actual speed is too fast. The indicator 210 can indicate the fast speed through corresponding light energy (such as a red light) as emitted by the light(s) 212, and/or an audio signal emitted through the speaker 214.

If, however, the actual speed of the wand assembly is too slow, thereby providing inefficient sanitization (for example, determined to be less than the correct speed or not within the acceptable range corresponding to the correct speed), the verification control unit 206 outputs an indication signal to the wand assembly 102 indicating that the actual speed is too slow. The indicator 210 can indicate the slow speed through corresponding light energy (such as a yellow light) as emitted by the light(s) 212, and/or an audio signal emitted through the speaker 214.

As described herein, the system 200 includes the wand assembly 102, which includes the sanitizing head 106 having the UV lamp 140 configured to emit UV light to sanitize a surface of a component. The wand assembly further includes the first monitored member 202. The system 200 also includes the second monitored member 204. The verification control unit 206 is in communication with the first monitored member 202 and the second monitored member 204. The verification control unit 206 is configured to detect a speed of the wand assembly 102 based on a comparison of the first monitored member 202 in relation to the second monitored member 204.

As an example, the verification control unit 206 determines whether or not the speed of the wand assembly 102 is sufficient to sanitize the surface based on a comparison of the speed of the wand assembly 102 and pacing data stored in the memory 208. The verification control unit 206 outputs an alert signal in response to the speed being outside of a defined range as set forth in the pacing data. The verification control unit 206 outputs a proper speed signal in response to the speed being within the define range as set forth in the pacing data.

In at least one embodiment, the wand assembly 102 further includes the indicator 210, which is configured to indicate a status of the speed of the wand assembly 102. For example, the indicator 210 includes at least one light 212 and/or a speaker 214.

In at least one embodiment, the results of a sanitation process, as performed by the wand assembly 102, can be recorded in the memory 208. For example, if the sanitation process is determined by the verification control unit 206 to be effective to sanitize one or more surfaces (as determined by the pacing speed at a particular range, for example), the effective sanitation process is stored and time stamped in the memory 208.

The wand speed verification system 100 verifies the speed of the wand assembly 102 to ensure that a correct dosage of sanitizing light, such as 222 nm UV light or 254 nm UV light, is delivered to a surface. In at least one embodiment, the second monitored member 204 is a radio frequency (RF) receiver located in a fixed position, such as on a location on an operator (for example, on the backpack assembly 104) or in a fixed location in an environment (such as within an internal cabin of a vehicle). In this embodiment, the first monitored member 202 is an RF emitter disposed on the wand assembly 102, such as on the sanitizing head 106. In at least one embodiment, the verification control unit 206 determines the speed of the wand assembly 102 by integrating the location of the sanitizing head 106 relative to the fixed location. The operator is informed of the actual wand speed by the indicator activity, which can include a pacing light or an audio tone on the wand assembly 102. Alternatively, the first monitored member 202 is the RF receiver, and the second monitored member 204 is in the fixed position.

Alternatively, the second monitored member 204 is a camera in the fixed location and, the first monitored member 202 is an optical target on the wand assembly 102 (such as on the sanitizing head 106). Optionally, the second monitored member 204 is the optical target, and the first monitored member 202 is the camera.

As another option, the second monitored member 204 is an infrared source on the fixed location and the first monitored member 202 is an infrared optical target located on the wand assembly 102. Optionally, the second monitored member 204 is the infrared optical target, and the first monitored member 202 is the infrared source.

As another option, the first monitored member 202 or the second monitored member 204 is a light detection and ranging (LIDAR) detector, and the other of the first monitored member 202 or the second monitored member 204 is a LIDAR optical target.

As another option, the first monitored member 202 is an accelerometer on or within the wand assembly 102. In this embodiment, the second monitored member 204 may not be necessary. Instead, the verification control unit 206 detects the speed of the wand assembly 102 through one or more signals output by the accelerometer.

In at least one embodiment, the speed of the wand assembly 102 is determined by the range to the surface for a wand of a certain lamp power. Once the operator selects the range (for example, 4 inches from the surface to disinfect), the verification control unit 206 determines the required speed to achieve the correct dosage of UV light, as stored in the memory 208 as pacing data.

In at least one embodiment, a predetermined dosage of UV light is determined by lamp power, range to target, and time of exposure. The speed of the wand assembly 102 determines the time of exposure.

As used herein, the term "control unit," "central processing unit," "CPU," "computer," or the like can include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the verification control unit 206 can be or include one or more processors that are configured to control operation, as described herein.

The verification control unit 206 is configured to execute a set of instructions that are stored in one or more data storage units or elements (such as one or more memories), in order to process data. For example, the verification control unit 206 may include or be coupled to one or more memories. The data storage units can also store data or other information as desired or needed. The data storage units can be in the form of an information source or a physical memory element within a processing machine.

The set of instructions may include various commands that instruct the verification control unit 206 as a processing machine to perform specific operations such as the methods and processes of the various embodiments of the subject matter described herein. The set of instructions can be in the form of a software program. The software can be in various forms such as system software or application software. Further, the software can be in the form of a collection of separate programs, a program subset within a larger program, or a portion of a program. The software can also include modular programming in the form of object-oriented programming. The processing of input data by the processing machine can be in response to user commands, or in response to results of previous processing, or in response to a request made by another processing machine.

The diagrams of embodiments herein can illustrate one or more control or processing units, such as the verification control unit 206. It is to be understood that the processing or control units can represent circuits, circuitry, or portions thereof that can be implemented as hardware with associated instructions (e.g., software stored on a tangible and non-transitory computer readable storage medium, such as a computer hard drive, ROM, RAM, or the like) that perform the operations described herein. The hardware can include state machine circuitry hardwired to perform the functions described herein. Optionally, the hardware can include electronic circuits that include and/or are connected to one or more logic-based devices, such as microprocessors, processors, controllers, or the like. Optionally, the verification control unit 206 can represent processing circuitry such as one or more of a field programmable gate array (FPGA), application specific integrated circuit (ASIC), microprocessor(s), and/or the like. The circuits in various embodiments can be configured to execute one or more algorithms to perform functions described herein. The one or more algorithms can include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 20:
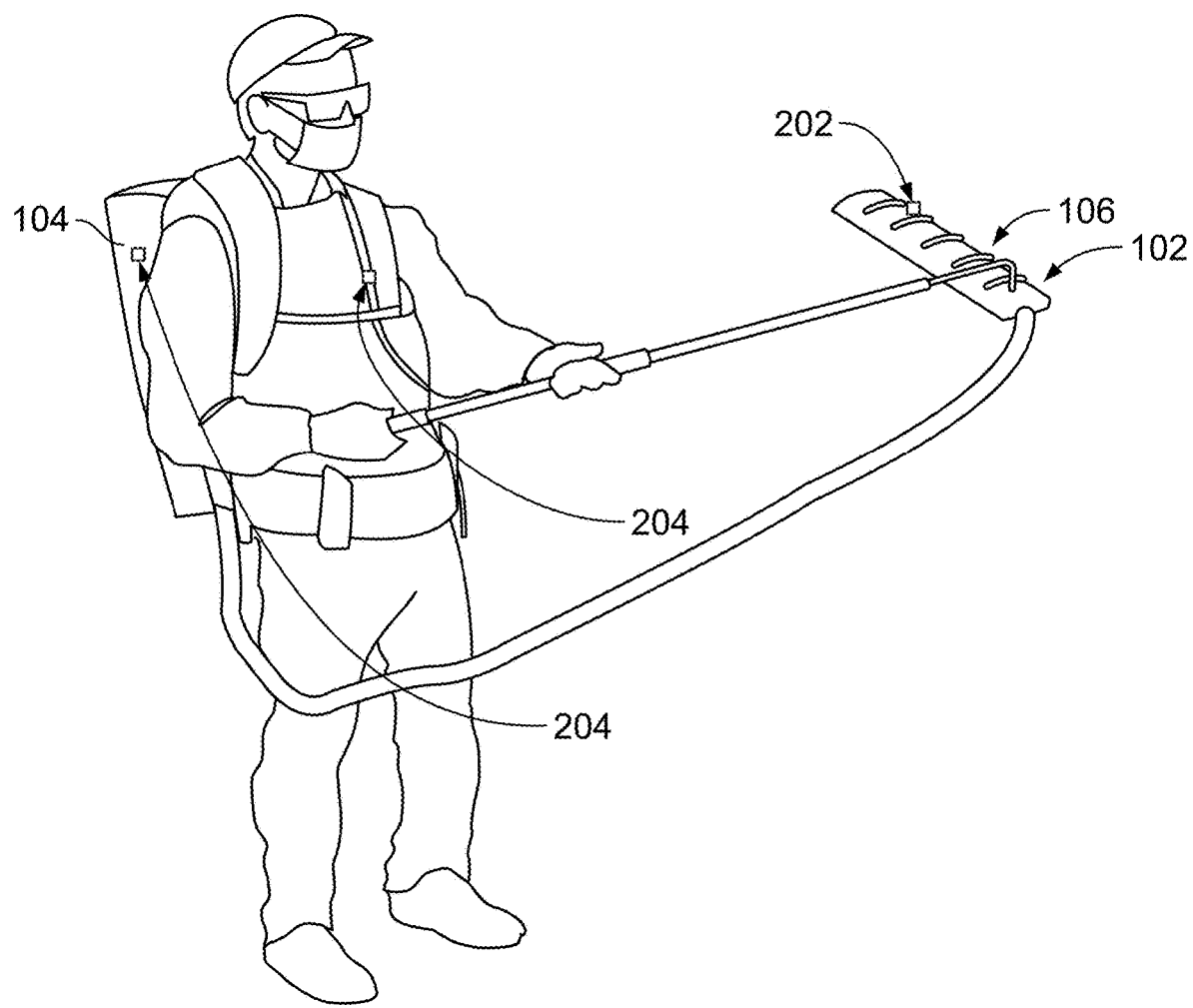
FIG. 20 illustrates a perspective view of a portable sanitizing system worn by an individual, according to an embodiment of the subject disclosure.

FIG. 20 illustrates a perspective view of a portable sanitizing system 100 worn by an individual 101, according to an embodiment of the subject disclosure. As shown, the first monitored member 202 is on the sanitizing head 106 of the wand assembly 102. The second monitored member 204 can be in the backpack assembly 104 and/or a portion of the harness 105.

Figure 21:
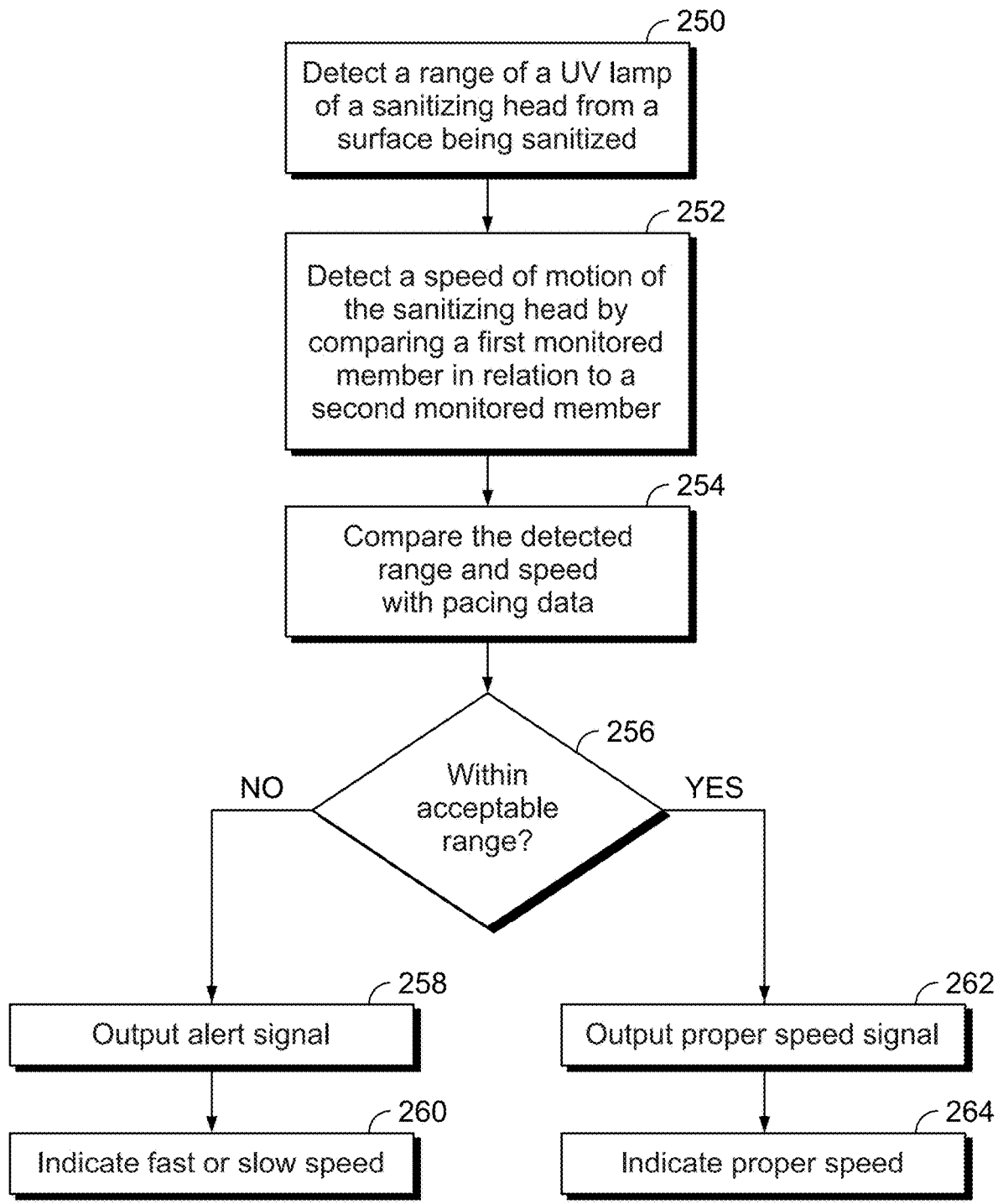
FIG. 21 illustrates a flow chart of a wand speed verification method, according to an embodiment of the subject disclosure.

FIG. 21 illustrates a flow chart of a wand speed verification method, according to an embodiment of the subject disclosure. Referring to FIGS. 19-21, at 250, the verification control unit 206 detects a range of the UV lamp 140 of the sanitizing head 106 from a surface being sanitized, such as via one or more range sensors of the sanitizing head 106. At 252, the verification control unit 206 detects a speed of motion of the sanitizing head 106 by comparing a change in position of the first monitored member 202 in relation to a position of the second monitored member 204 over time.

At 254, the verification control unit 206 compares the detected range and speed of the sanitizing head 106 with the pacing data stored in the memory 208. At 256, the verification control unit 206 determines whether the detected range and speed are within an acceptable range (such as within +/−5%) of the pacing data. If not, the method proceeds from 256 to 258, at which the verification control unit 206 outputs an alert signal to the wand assembly 102. At 260, the alert signal is indicated on the indicator 210, which indicates a corresponding fast or slow speed.

If, however, the verification control unit 206 determines that the detected range and speed are within the acceptable range, the method proceeds from 256 to 262, at which the verification control unit 206 outputs a proper speed signal to the wand assembly 102. At 264, the proper speed signal is indicated on the indicator 210, which indicates a corresponding proper speed for sanitization.

Figure 22:
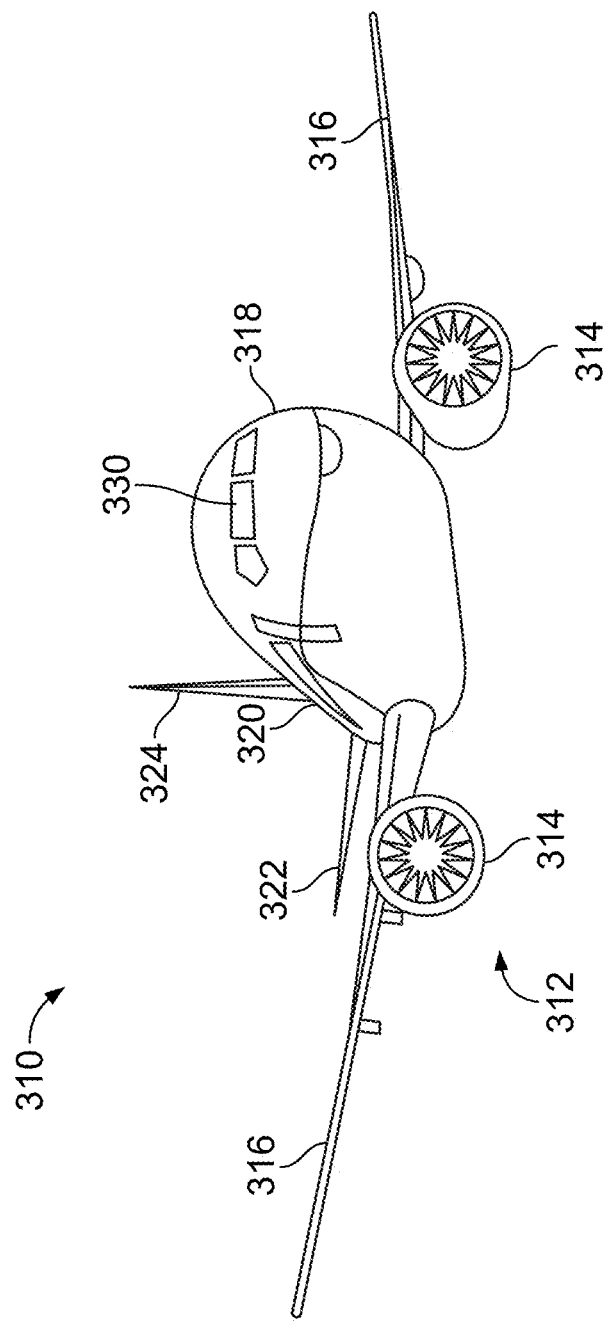
FIG. 22 illustrates a perspective front view of an aircraft, according to an embodiment of the subject disclosure.

FIG. 22 illustrates a perspective front view of an aircraft 310, according to an embodiment of the subject disclosure. The aircraft 310 includes a propulsion system 312 that includes engines 314, for example. Optionally, the propulsion system 312 can include more engines 314 than shown. The engines 314 are carried by wings 316 of the aircraft 310. In other embodiments, the engines 314 can be carried by a fuselage 318 and/or an empennage 320. The empennage 320 can also support horizontal stabilizers 322 and a vertical stabilizer 324.

The fuselage 318 of the aircraft 310 defines an internal cabin 330, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 330 includes one or more lavatory systems, lavatory units, or lavatories, as described herein.

Alternatively, instead of an aircraft, embodiments of the subject disclosure can be used with various other vehicles, such as automobiles, buses, locomotives and train cars, watercraft, and the like. Further, embodiments of the subject disclosure may be used with respect to fixed structures, such as commercial and residential buildings (for example, theaters, concert venues, auditoriums, classrooms, stadiums, grocery stores, office buildings, hospitals, and the like).

Figure 23A:
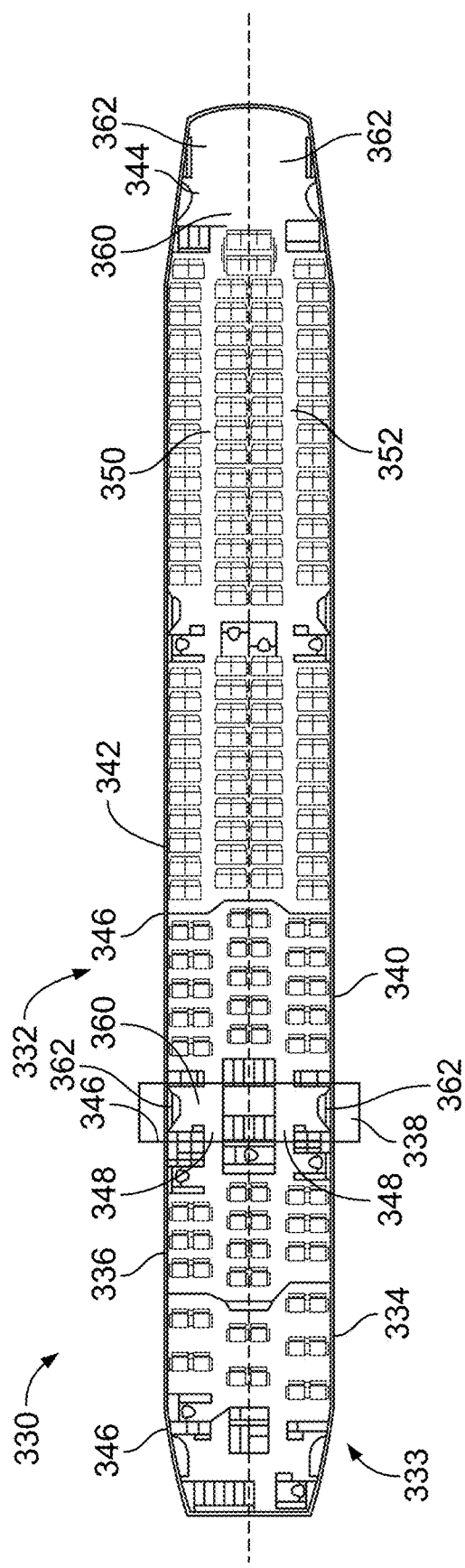
FIG. 23A illustrates a top plan view of an internal cabin of an aircraft, according to an embodiment of the subject disclosure.

FIG. 23A illustrates a top plan view of an internal cabin 330 of an aircraft, according to an embodiment of the subject disclosure. The internal cabin 330 can be within the fuselage 332 of the aircraft, such as the fuselage 318 of FIG. 227. For example, one or more fuselage walls can define the internal cabin 330. The internal cabin 330 includes multiple sections, including a front section 333, a first class section 334, a business class section 336, a front galley station 338, an expanded economy or coach section 340, a standard economy of coach section 342, and an aft section 344, which may include multiple lavatories and galley stations. It is to be understood that the internal cabin 330 can include more or less sections than shown. For example, the internal cabin 330 may not include a first class section, and can include more or less galley stations than shown. Each of the sections can be separated by a cabin transition area 346, which can include class divider assemblies between aisles 348.

As shown in FIG. 23A, the internal cabin 330 includes two aisles 350 and 352 that lead to the aft section 344. Optionally, the internal cabin 330 can have less or more aisles than shown. For example, the internal cabin 330 can include a single aisle that extends through the center of the internal cabin 330 that leads to the aft section 344.

The aisles 348, 350, and 352 extend to egress paths or door passageways 360. Exit doors 362 are located at ends of the egress paths 360. The egress paths 360 can be perpendicular to the aisles 348, 350, and 352. The internal cabin 330 can include more egress paths 360 at different locations than shown. The portable sanitizing system 100 shown and described with respect to FIGS. 1-21 can be used to sanitize various structures within the internal cabin 330, such as passenger seats, monuments, stowage bin assemblies, components on and within lavatories, galley equipment and components, and/or the like.

Figure 23B:
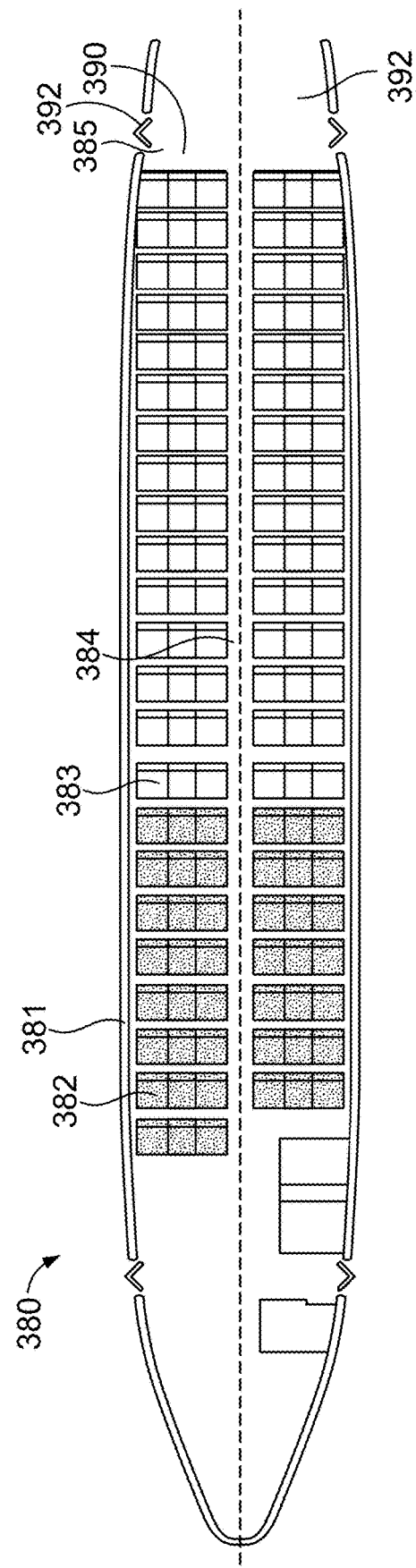
FIG. 23B illustrates a top plan view of an internal cabin of an aircraft, according to an embodiment of the subject disclosure.

FIG. 23B illustrates a top plan view of an internal cabin 380 of an aircraft, according to an embodiment of the subject disclosure. The internal cabin 380 is an example of the internal cabin 330 shown in FIG. 22. The internal cabin 380 can be within a fuselage 381 of the aircraft. For example, one or more fuselage walls can define the internal cabin 380. The internal cabin 380 includes multiple sections, including a main cabin 382 having passenger seats 383, and an aft section 385 behind the main cabin 382. It is to be understood that the internal cabin 380 can include more or less sections than shown.

The internal cabin 380 can include a single aisle 384 that leads to the aft section 385. The single aisle 384 can extend through the center of the internal cabin 380 that leads to the aft section 385. For example, the single aisle 384 can be coaxially aligned with a central longitudinal plane of the internal cabin 380.

The aisle 384 extends to an egress path or door passageway 390. Exit doors 392 are located at ends of the egress path 390. The egress path 390 can be perpendicular to the aisle 384. The internal cabin 380 can include more egress paths than shown. The portable sanitizing system 100 shown and described with respect to FIGS. 1-21 can be used to sanitize various structures within the internal cabin 330, such as passenger seats, monuments, stowage bin assemblies, components on and within lavatories, galley equipment and components, and/or the like.

Figure 24:
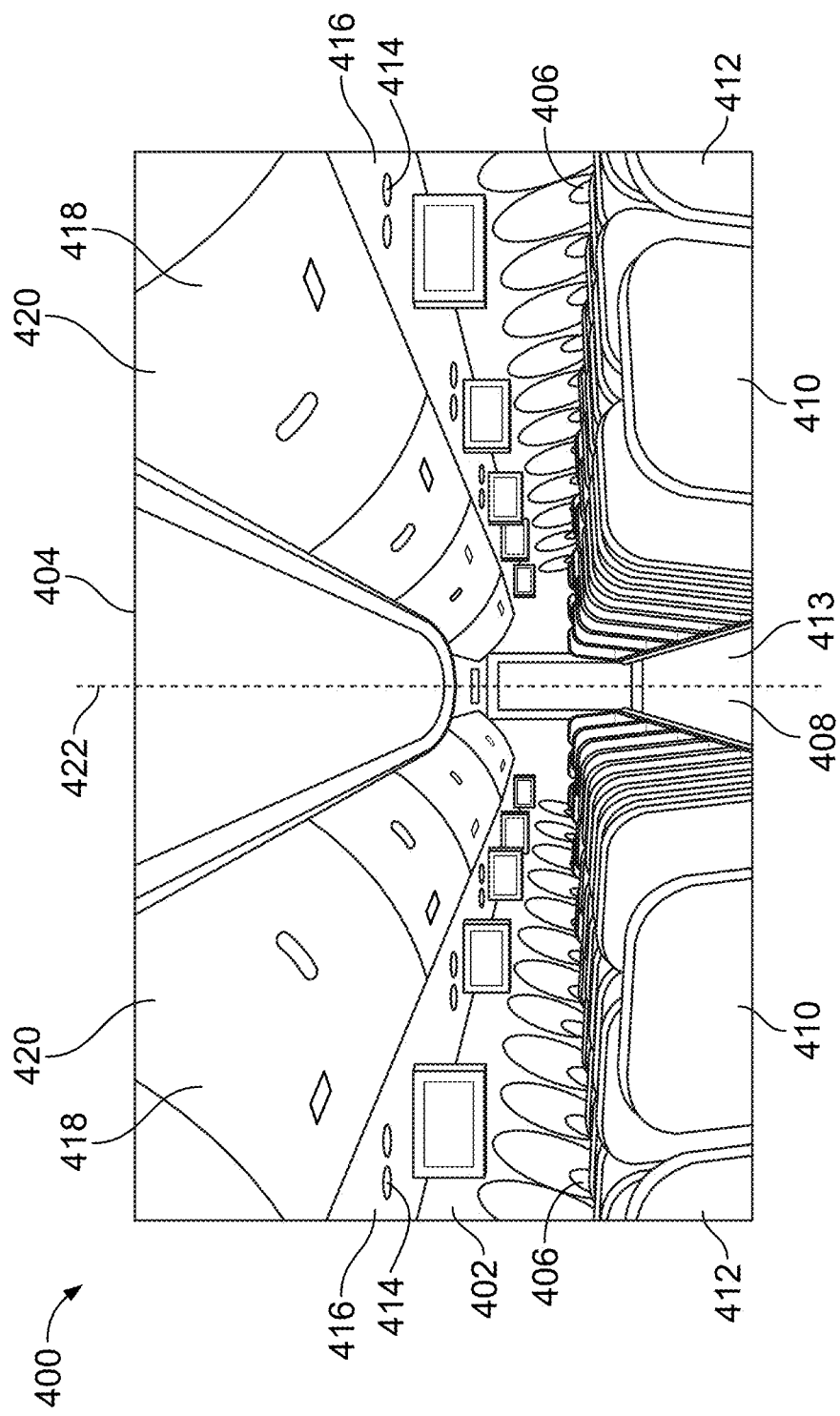
FIG. 24 illustrates a perspective interior view of an internal cabin of an aircraft, according to an embodiment of the subject disclosure.

FIG. 24 illustrates a perspective interior view of an internal cabin 400 of an aircraft, according to an embodiment of the subject disclosure. The internal cabin 400 includes outboard walls 402 connected to a ceiling 404. Windows 406 can be formed within the outboard walls 402. A floor 408 supports rows of seats 410. As shown in FIG. 24, a row 412 can include two seats 410 on either side of an aisle 413. However, the row 412 can include more or less seats 410 than shown. Additionally, the internal cabin 400 can include more aisles than shown.

Passenger service units (PSUs) 414 are secured between an outboard wall 402 and the ceiling 404 on either side of the aisle 413. The PSUs 414 extend between a front end and rear end of the internal cabin 400. For example, a PSU 414 can be positioned over each seat 410 within a row 412. Each PSU 414 can include a housing 416 that generally contains vents, reading lights, an oxygen bag drop panel, an attendant request button, and other such controls over each seat 410 (or groups of seats) within a row 412.

Overhead stowage bin assemblies 418 are secured to the ceiling 404 and/or the outboard wall 402 above and inboard from the PSU 414 on either side of the aisle 413. The overhead stowage bin assemblies 418 are secured over the seats 410. The overhead stowage bin assemblies 418 extend between the front and rear end of the internal cabin 400. Each stowage bin assembly 418 can include a pivot bin or bucket 420 pivotally secured to a strongback (hidden from view in FIG. 24). The overhead stowage bin assemblies 418 can be positioned above and inboard from lower surfaces of the PSUs 414. The overhead stowage bin assemblies 418 are configured to be pivoted open in order to receive passenger carry-on baggage and personal items, for example.

As used herein, the term "outboard" means a position that is further away from a central longitudinal plane 422 of the internal cabin 400 as compared to another component. The term "inboard" means a position that is closer to the central longitudinal plane 422 of the internal cabin 400 as compared to another component. For example, a lower surface of a PSU 414 may be outboard in relation to a stowage bin assembly 418.

The portable sanitizing system 100 shown and described with respect to FIGS. 1-21 can be used to sanitize various structures shown within the internal cabin 400.

When not in use, the portable sanitizing system 100 can be stored within a closet, galley cart bay, or galley cart, such as within the internal cabin of the vehicle.

Figure 25:
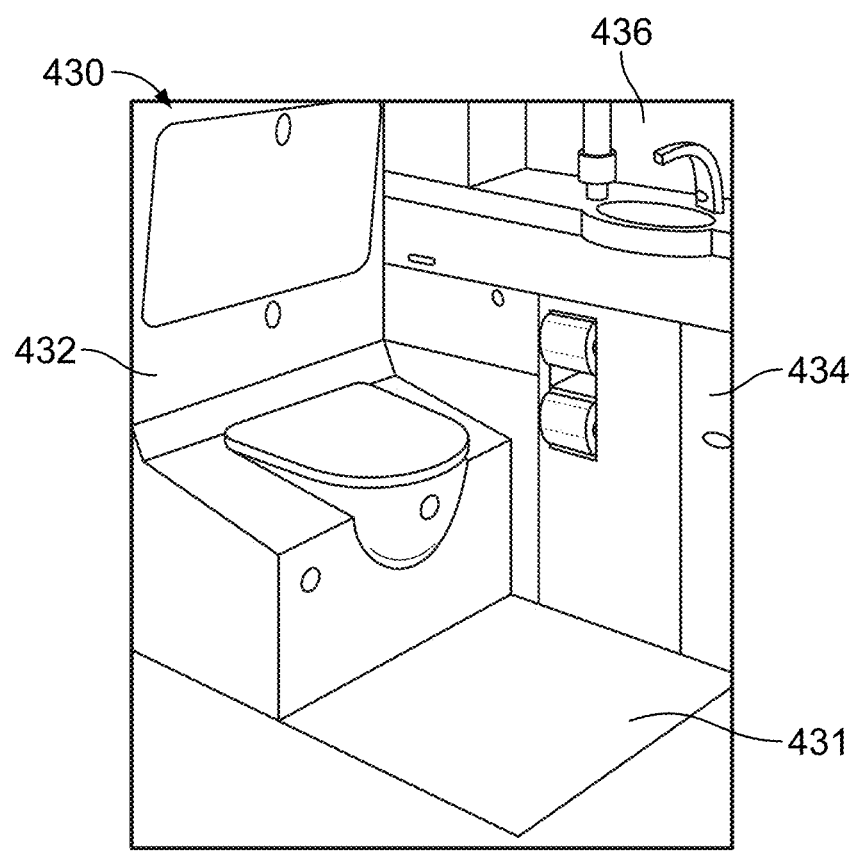
FIG. 25 illustrates a perspective internal view of a lavatory within an internal cabin of an aircraft.

FIG. 25 illustrates a perspective internal view of a lavatory 430 within an internal cabin of a vehicle, such as any of the internal cabins described herein. The lavatory 430 is an example of an enclosed space, monument or chamber, such as within the internal cabin a vehicle. The lavatory 430 can be onboard an aircraft, as described above. Optionally, the lavatory 430 can be onboard various other vehicles. In other embodiments, the lavatory 430 can be within a fixed structure, such as a commercial or residential building. The lavatory 430 includes a base floor 431 that supports a toilet 432, cabinets 434, and a sink 436 or wash basin. The lavatory 430 can be arranged differently than shown. The lavatory 430 can include more or less components than shown. The portable sanitizing system 100 shown and described with respect to FIGS. 1-21 can be used to sanitize the various structures, components, and surfaces within the lavatory 430.

The portable sanitizing systems 100 as described herein can be used to safely and effectively sanitize high-touch surfaces in the flight deck and internal cabin in a timely and cost-effective manner. UV disinfection allows the internal cabin to be quickly and effectively disinfected, such as between flights. In at least one embodiment, the portable sanitizing system 100 is used to augment a cleaning process, such as after manual cleaning.

As described herein, embodiments of the subject disclosure provide systems and a methods for efficiently sterilizing surfaces, components, structures, and/or the like within an internal cabin of a vehicle. Further, embodiments of the subject disclosure provide compact, easy-to-use, and safe systems and methods for using UV light to sterilize surfaces within an internal cabin.

Further, certain embodiments of the subject disclosure provide systems and methods to verify that motion of a wand assembly having a UV lamp is sufficient to sanitize a surface of a component. Further, the systems and methods ensure the correct dosage of UV light is delivered to a surface to effectively sanitize the surface.

Further, the disclosure comprises embodiments according to the following clauses:

Clause 1. A system comprising:

a wand assembly including a sanitizing head having an ultraviolet (UV) lamp configured to emit UV light to sanitize a surface of a component, the wand assembly further including a first monitored member;

a second monitored member; and a verification control unit in communication with one or both of the first monitored member or the second monitored member, wherein the verification control unit is configured to detect a speed of the wand assembly based on a comparison of the first monitored member in relation to the second monitored member.

Clause 2. The system of Clause 1, wherein the verification control unit determines whether or not the speed of the wand assembly is sufficient to sanitize the surface based on a comparison of the speed of the wand assembly and pacing data stored in memory.

Clause 3. The system of Clauses 1 or 2, wherein the verification control unit outputs an alert signal in response to the speed being outside of a defined range as set forth in the pacing data.

Clause 4. The system of any of Clauses 1-3, wherein the verification control unit outputs a proper speed signal in response to the speed being within the define range as set forth in the pacing data.

Clause 5. The system of any of Clauses 1-4, wherein the wand assembly further comprises an indicator that is configured to indicate a status of the speed of the wand assembly.

Clause 6. The system of Clause 5, wherein the indicator comprises at least one of a display, a light, a vibration motor, or a speaker.

Clause 7. The system of any of Clauses 1-6, wherein the second monitored member is secured to a fixed structure within an internal cabin of a vehicle.

Clause 8. The system of any of Clauses 1-7, wherein the second monitored member is secured to a portion of a backpack assembly that is coupled to the wand assembly.

Clause 9. The system of Clause 8, wherein one of the wand assembly, a backpack assembly, or a case assembly comprises the verification control unit.

Clause 10. The system of any of Clauses 1-9, wherein the verification control unit compares the speed of the wand assembly at a range from the surface in relation to pacing data stored in a memory to determine whether or not the speed of the wand assembly is sufficient to sanitize the surface.

Clause 11. The system of any of Clauses 1-10, wherein one of the first monitored member or the second monitored member is a radio frequency (RF) receiver, and wherein the other of the first monitored member or the second monitored member is an RF emitter.

Clause 12. The system of any of Clauses 1-7, 10, or 11, wherein one of the first monitored member or the second monitored member is a camera, and wherein the other of the first monitored member or the second monitored member is an optical target.

Clause 13. The system of any of Clauses 1-7, 10, or 11, wherein one of the first monitored member or the second monitored member is an infrared source, and wherein the other of the first monitored member or the second monitored member is an infrared optical target.

Clause 14. The system of any of Clauses 1-7, 10, or 11, wherein one of the first monitored member or the second monitored member is a LIDAR detector, and the other of the first monitored member or the second monitored member is a LIDAR optical target.

Clause 15. The system of any of Clauses 1-7, 10 or 11, wherein the first monitored member is an accelerometer.

Clause 16. The system of any of Clauses 1-15, wherein the UV lamp is configured to emit the UV light at a wavelength of 222 nm.

Clause 17. The system of any of Clauses 1-15, wherein the UV lamp is configured to emit the UV light within a far UV spectrum.

Clause 18. The system of any of Clauses 1-15, wherein the UV lamp is configured to emit the UV light at a wavelength of 254 nm.

Clause 19. The system of any of Clauses 1-15, wherein the UV lamp is configured to emit the UV light within a UVC spectrum.

Clause 20. A method comprising:
employing a wand assembly including a sanitizing head having an ultraviolet (UV) lamp configured to emit UV light to sanitize a surface of a component, the wand assembly further including a first monitored member;
communicatively coupling a verification control unit with one or both of the first monitored member or a second monitored member; and
detecting, by the verification control unit, a speed of the wand assembly based on a comparison of the first monitored member in relation to the second monitored member.

Clause 21. The method of Clause 20, further comprising determining, by the verification control unit, whether or not the speed of the wand assembly is sufficient to sanitize the surface based on a comparison of the speed of the wand assembly and pacing data stored in memory.

Clause 22. The method of Clause 21, further comprising outputting, by the verification control unit, an alert signal in response to the speed being outside of a defined range as set forth in the pacing data.

Clause 23. The method of any of Clauses 20-22, further comprising outputting, by the verification control unit, a proper speed signal in response to the speed being within the define range as set forth in the pacing data.

Clause 24. The method of any of Clauses 20-23, further comprising indicating, by an indicator of the wand assembly, a status of the speed of the wand assembly.

Clause 25. The method of any of Clauses 20-24, further comprising securing the second monitored member to a fixed structure within an internal cabin of a vehicle.

Clause 26. The method of any of Clauses 20-25, further comprising securing the second monitored member to a portion of a backpack assembly or case assembly that is coupled to the wand assembly.

Clause 27. The method of any of Clauses 20-26, further comprising comparing, by the verification control unit, the speed of the wand assembly at a range from the surface in relation to pacing data stored in a memory to determine whether or not the speed of the wand assembly is sufficient to sanitize the surface.

Clause 28. A system comprising:
a first monitored member configured to be coupled to a wand assembly comprising a sanitizing head having an ultraviolet (UV) lamp configured to emit UV light to sanitize a surface of a component;
a second monitored member; and
a verification control unit in communication with one or both of the first monitored member or the second monitored member, wherein the verification control unit is configured to detect a speed of the wand assembly based on a comparison of the first monitored member in relation to the second monitored member.

While various spatial and directional terms, such as top, bottom, lower, mid, lateral, horizontal, vertical, front and the like can be used to describe embodiments of the subject disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "containing" are used as the plain-English equivalents of the term "comprising" and the term "in which" is used as the plain-English equivalents of the term "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system comprising:
a wand assembly comprising a sanitizing head having an ultraviolet (UV) lamp configured to emit UV light to sanitize a surface, the wand assembly further comprising a first monitored member;
a second monitored member secured to a portion of a backpack assembly that is coupled to the wand assembly, wherein the second monitored member is separate and distinct from the first monitored member, wherein one or both of the first monitored member or the second monitored member is configured to output one or more signals; and
a verification control unit in communication with one or both of the first monitored member or the second monitored member, wherein the verification control unit is configured to detect a speed of the wand assembly based on a comparison of a position of the first monitored member in relation to a position of the second monitored member.

2. The system of claim 1, wherein the verification control unit determines whether or not the speed of the wand assembly is sufficient to sanitize the surface based on a comparison of the speed of the wand assembly and pacing data.

3. The system of claim 2, wherein the verification control unit outputs an alert signal in response to the speed being outside of a defined range as set forth in the pacing data.

4. The system of claim 3, wherein the verification control unit outputs a proper speed signal in response to the speed being within the defined range as set forth in the pacing data.

5. The system of claim 1, wherein the wand assembly further comprises an indicator that is configured to indicate a status of the speed of the wand assembly.

6. The system of claim 5, wherein the indicator comprises at least one of a display, a light, a vibration motor, or a speaker.

7. The system of claim 1, wherein one of the wand assembly, a backpack assembly, or a case assembly comprises the verification control unit.

8. The system of claim 1, wherein the verification control unit compares the speed of the wand assembly at a range from the surface in relation to pacing data stored in a memory to determine whether or not the speed of the wand assembly is sufficient to sanitize the surface.

9. The system of claim 1, wherein one of the first monitored member or the second monitored member is a radio frequency (RF) receiver, and wherein the other of the first monitored member or the second monitored member is an RF emitter.

10. The system of claim 1, wherein one of the first monitored member or the second monitored member is a camera, and wherein the other of the first monitored member or the second monitored member is an optical target.

11. The system of claim 1, wherein one of the first monitored member or the second monitored member is an infrared source, and wherein the other of the first monitored member or the second monitored member is an infrared optical target.

12. The system of claim 1, wherein one of the first monitored member or the second monitored member is a LIDAR detector, and the other of the first monitored member or the second monitored member is a LIDAR optical target.

13. The system of claim 1, wherein the first monitored member is an accelerometer.

14. The system of claim 1, wherein the UV lamp is configured to emit the UV light at a wavelength of 222 nm.

15. The system of claim 1, wherein the UV lamp is configured to emit the UV light within a far UV spectrum.

16. The system of claim 1, wherein the UV lamp is configured to emit the UV light at a wavelength of 254 nm.

17. The system of claim 1, wherein the UV lamp is configured to emit the UV light within a UVC spectrum.

18. The system of claim 1, wherein the first monitored member is configured to output one or more first signals, and the second monitored member is configured to output one or more second signals, wherein the verification control unit is in communication with both of the first monitored member and the second monitored member, and wherein the verification control unit is configured to detect the speed of the wand assembly based on a comparison of the one or more first signals output by the first monitored member in relation to the one or more second signals output by the second monitored member.

19. A method for a system comprising:
 a wand assembly comprising a sanitizing head having an ultraviolet (UV) lamp configured to emit UV light to sanitize a surface, the wand assembly further comprising a first monitored member;
 a second monitored member secured to a portion of a backpack assembly that is coupled to the wand assembly, wherein the second monitored member is separate and distinct from the first monitored member, wherein one or both of the first monitored member or the second monitored member is configured to output one or more signals; and
 a verification control unit in communication with the first monitored member and the second monitored member, wherein the verification control unit is configured to detect a speed of the wand assembly based on a comparison of a position of the first monitored member in relation to a position of the second monitored member,
 the method comprising:
 employing the wand assembly to sanitize the surface;
 communicatively coupling the verification control unit with one or both of the first monitored member or the second monitored member; and
 detecting, by the verification control unit, the speed of the wand assembly based on the comparison of the position of the first monitored member in relation to the position of the second monitored member.

20. The method of claim 19, further comprising:
 determining, by the verification control unit, whether or not the speed of the wand assembly is sufficient to sanitize the surface based on a comparison of the speed of the wand assembly and pacing data stored in memory;
 outputting, by the verification control unit, an alert signal in response to the speed being outside of a defined range as set forth in the pacing data;
 outputting, by the verification control unit, a proper speed signal in response to the speed being within the defined range as set forth in the pacing data; and
 indicating, by an indicator of the wand assembly, a status of the speed of the wand assembly.

21. The method of claim 19, further comprising comparing, by the verification control unit, the speed of the wand assembly at a range from the surface in relation to pacing data stored in a memory to determine whether or not the speed of the wand assembly is sufficient to sanitize the surface.

22. A system comprising:
 a first monitored member configured to be coupled to a wand assembly comprising a sanitizing head having an ultraviolet (UV) lamp configured to emit UV light to sanitize a surface, wherein the first monitored member is a radio frequency (RF) receiver or an RF emitter;
 a second monitored member that is separate and distinct from the first monitored member, wherein one or both of the first monitored member or the second monitored member is configured to output one or more signals, and wherein the second monitored member is the other of the RF receiver or the RF emitter; and
 a verification control unit in communication with one or both of the first monitored member or the second monitored member, wherein the verification control unit is configured to detect a speed of the wand assembly based on a comparison of a first-position of the first monitored member in relation to a second position of the second monitored member.

23. The system of claim 22, wherein the verification control unit determines whether or not the speed of the wand assembly is sufficient to sanitize the surface based on a comparison of the speed of the wand assembly and pacing data.

24. The system of claim 23, wherein the verification control unit outputs an alert signal in response to the speed being outside of a defined range as set forth in the pacing data.

25. The system of claim 24, wherein the verification control unit outputs a proper speed signal in response to the speed being within the defined range as set forth in the pacing data.

* * * * *